(12) United States Patent
Khonsari et al.

(10) Patent No.: US 9,476,815 B2
(45) Date of Patent: Oct. 25, 2016

(54) FATIGUE MONITORING FOR COMPOSITE MATERIALS

(75) Inventors: Michael M. Khonsari, Baton Rouge, LA (US); Mehdi Naderi Abadi, Miami, FL (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 506 days.

(21) Appl. No.: 13/985,680

(22) PCT Filed: Feb. 16, 2012

(86) PCT No.: PCT/US2012/025383
§ 371 (c)(1),
(2), (4) Date: Nov. 18, 2013

(87) PCT Pub. No.: WO2013/105995
PCT Pub. Date: Jul. 18, 2013

(65) Prior Publication Data
US 2014/0067285 A1  Mar. 6, 2014

Related U.S. Application Data

(60) Provisional application No. 61/446,845, filed on Feb. 25, 2011.

(51) Int. Cl.
*G01B 3/44* (2006.01)
*G01N 3/32* (2006.01)

(52) U.S. Cl.
CPC ......... *G01N 3/32* (2013.01); *G01N 2203/0096* (2013.01); *G01N 2203/0694* (2013.01)

(58) Field of Classification Search
CPC ..................................................... G01N 3/32
USPC .................................................... 702/34
See application file for complete search history.

(56) References Cited

U.S. PATENT DOCUMENTS

| 8,209,133 B2 | 6/2012 | Khonsari | 702/34 |
| 2012/0084019 A1 | 4/2012 | Khonsari | 702/35 |

OTHER PUBLICATIONS

Fargione et al.; "Rapid determination of the fatigue curve by the thermographic method", 2002, International Journal of Fatigue, pp. 11-19.*
Meneghetti, "Analysis of the fatigue strength of a stainless steel based on the energy dissipation", 2007, International Journal of Fatigue, pp. 81-94.*
Amiri, M. et al., "On the role of entropy generation in processes involving fatigue," Entropy, vol. 14, pp. 24-31 (2012).

(Continued)

*Primary Examiner* — Sujoy Kundu
*Assistant Examiner* — Ricky Ngon
(74) *Attorney, Agent, or Firm* — John H. Runnels

(57) ABSTRACT

Fatigue failure in composite materials can be successfully modeled and predicted by monitoring irreversible gains in entropy. Permanent degradations in composites are marked by irreversible processes that are characterized by increases in entropy. By measuring changes in entropy, one can model and predict the deterioration and failure of composites. The technique may be used to predict the deterioration and failure of composites under essentially any type of loading—constant, variable, bending, torsion, tension, compression, or other.

1 Claim, 23 Drawing Sheets

(56) References Cited

OTHER PUBLICATIONS

Giancane, S. et al., "Characterization of fatigue damage in long fiber epoxy composite laminates," International Journal of Fatigue, vol. 32, pp. 46-53 (2010).

Naderi M. et al., "On the thermodynamic entropy of fatigue fracture," Proc. Roy. Soc. A., vol. 466, pp. 423-438 (2010).

Naderi, M. et al., "A Comprehensive Fatigue Failure Criterion Based on Thermodynamic Approach," J. Compos. Mat., vol. 46, pp. 437-447 (2012).

Naderi, M. et al., "Real-time Fatigue Life Monitoring based on Thermodynamic Entropy," Journal of Structure Health Monitoring, vol. 10, pp. 189-197 (2010).

Naderi, M. et al., "Thermodynamic Analysis of Fatigue Fatigue in a Composite Laminate," Mechanics of Materials, vol. 46, pp. 113-122 (2012).

Naderi, M. et al., "Dissipated Thermal Energy and Damage Evolution of Glass/Epoxy Using Infrared Thermography and Acoustic Emission," Composites Part B: Engineering, dx.doi.org/10.1016/j.compositesb.2011.08.002 (2011).

Natarajan, V. et al., "Fatigue response of fabric-reinforced polymeric composites," Journal of Composite Materials, vol. 39, pp. 1541-1559 (2005).

Petermann, J. et al., "A unified fatigue failure criterion for unidirectional laminates," Composites Part A—Applied Science and Manufacturing, vol. 32, pp. 107-118 (2001).

Reis, P. et al., "Fatigue Damage Characterization by NDT in Polypropylene/Glass Fibre Composites," Appl. Compos. Mater., vol. 18, pp. 409-419 (2010).

Shokrieh, M.M. et al., "A unified fatigue life model based on energy method," Composite Structures, vol. 75, pp. 444-450 (2006).

Toubal, L. et al., "Damage evolution and infrared thermography in woven composite laminates under fatigue loading," Int'l J. of Fatigue, vol. 28, pp. 1867-1872 (2006).

Varvani-Farahani, A. et al., "An energy-based fatigue damage parameter for off-axis unidirectional FRP composites," Composite Structures, vol. 79, pp. 381-389 (2007).

\* cited by examiner

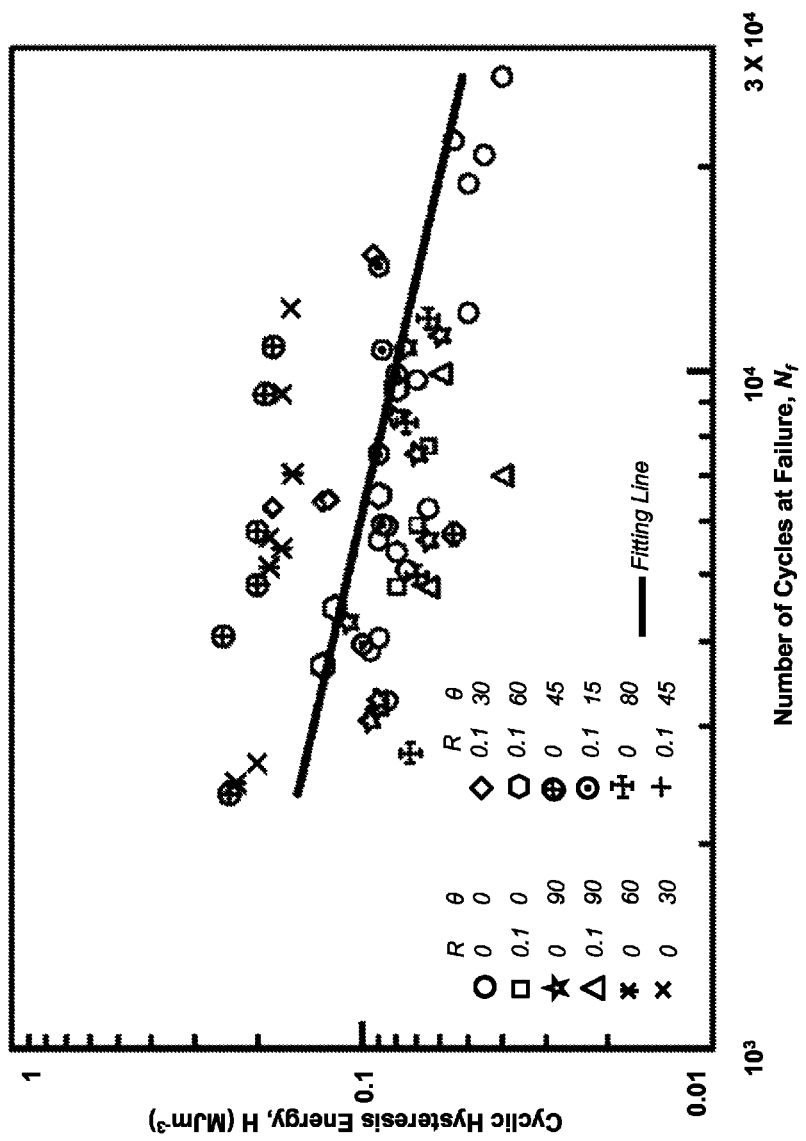

FATIGUE MONITORING FOR COMPOSITE MATERIALS

This is the United States national stage of international application PCT/US2012/025383, international filing date Feb. 16, 2012, which claims the benefit of the Feb. 25, 2011 filing date of U.S. provisional patent application Ser. No. 61/446,845 under 35 U.S.C. §119(e). The complete disclosure of the 61/446,845 priority application is hereby incorporated by reference in its entirety.

TECHNICAL FIELD

This invention pertains to the fatigue monitoring of composite materials.

BACKGROUND ART

Composite materials are widely used owing to their high strength and stiffness, low weight, and long fatigue life. Most composite materials are anisotropic and inhomogeneous, and thus exhibit significantly more complicated behaviors over their lifetimes than those of simple metals, particularly during repetitive cyclic loadings. For example, the fatigue behavior of a composite laminate is typically characterized by a combination of processes that have no counterparts in the behaviors of metals, such as matrix cracking, delamination, fiber-matrix debonding, and fiber breakage. The complex, multiple mechanisms by which composites can fatigue and fail has made it difficult to model, predict, and monitor fatigue damage in composite materials. Two prior approaches to evaluating fatigue life are the linear elastic strain energy life (W-N) model, and the hysteresis energy life model.

One approach is that of Shokrieh, M. M., and Taheri-Behrooz, F. 2006. A unified fatigue life model based on energy method, *Composite Structures*, 75:444-50. This fatigue life model was based on strain energy, and applied the model to on- and off-axis, unidirectional polymer-composite laminates subjected to tension-tension and compression-compression fatigue loading. Assuming that the stress-strain relation was elastic, the strain energy was normalized (with respect to the maximum monotonic strain energy, i.e., the product of the maximum monotonic stress and strain) to indirectly take into account the fiber orientation angle, yielding the relation:

$$\Delta W = \frac{1}{X\varepsilon_{1u}}\left(\frac{\sigma_{1max}\varepsilon_{1max} -}{\sigma_{1min}\varepsilon_{1min}}\right) + \frac{1}{Y\varepsilon_{2u}}\left(\frac{\sigma_{2max}\varepsilon_{2max} -}{\sigma_{2min}\varepsilon_{2min}}\right) + \frac{1}{S\varepsilon_{6u}}\left(\frac{\sigma_{6max}\varepsilon_{6max} -}{\sigma_{6min}\varepsilon_{6min}}\right) \quad (1)$$

where $\Delta W$ is the normalized linear elastic strain energy; $\sigma_{1max}$, $\sigma_{2max}$, $\sigma_{6max}$, $\sigma_{1min}$, $\sigma_{2min}$, $\sigma_{6min}$ are the maximum and minimum stress components; and $\varepsilon_{1max}$, $\varepsilon_{2max}$, $\varepsilon_{6max}$, $\varepsilon_{1min}$, $\varepsilon_{2min}$, $\varepsilon_{6min}$ are the corresponding maximum and minimum strain components in the fiber directions. X, Y, and S are the maximum static strength in the lengthwise and crosswise directions, and the shear strength, respectively. $\varepsilon_{1u}$, $\varepsilon_{2u}$, $\varepsilon_{6u}$ are the ultimate strains in the monotonic test. In a tension-tension fatigue test, when the 0° fibers are under tension the 90° fibers are under compression. Therefore, the value of compressive strength should be used in Equation (1) to evaluate strain energy. Since the specimens used were thin, the value of the 90° edgewise compressive strength, which is equal to the 90° tensile strength, was used in Equation (1) to calculate strain energy. Taking advantage of the transformation relationships between the on- and off-axis stress and using the linear elastic assumption, Equation (1) becomes $$\Delta W = \frac{1+R}{1-R}\Delta\sigma^2\left(\frac{\cos^4\theta}{X^2} + \frac{\sin^4\theta}{Y^2} + \frac{\sin^2\theta\cos^2\theta}{S^2}\right) \quad (2)$$

where R is the stress ratio $$\left(R = \frac{\sigma_{min}}{\sigma_{max}}\right),$$

$\Delta\sigma$ represents the stress range ($\Delta\sigma = \sigma_{max} - \sigma_{min}$), and $\theta$ denotes the angle between the lengthwise fibers and the load direction.

Measuring the experimental stress range then allows one to calculate the elastic strain energy density at different number of cycles at failure ($N_f$).

Another approach is that of Giancane, S., Panella, F. W., and Dattoma, V. 2010. Characterization of fatigue damage in long fiber epoxy composite laminates, *International Journal of Fatigue*, 32:46-53; and Petermann, J., and Plumtree, A. 2001. A unified fatigue failure criterion for unidirectional laminates, *Composites Part A-Applied Science and Manufacturing*, 32:107-18. This hysteresis energy life model is based on the hysteresis area under cyclic loading (H)—a quantity that represents dissipated energy. The hysteresis area increases during the fatigue process as the result of permanent deformation. The hysteresis energy has two components: one that is released during the unloading process, and a second that represents the damage energy responsible for the creation of new cracks and the propagation of the existing cracks. The cyclic hysteresis energy may be directly calculated from the experimental stress and strain measurements in real time as:

$$H = \sum_{i=1}^{n}(\sigma_i - \sigma_{i-1})(\varepsilon_i - \varepsilon_{i-1}) \quad (3)$$

where n is the number of points acquired per cycle during fatigue. The total hysteresis energy or accumulated fracture energy, $w_t$, at failure is obtained by summing the hysteresis energy per cycle over the total number of cycles to failure, $N_f$.

$$w_t = \sum_{j=1}^{N_f}\left(\sum_{i=1}^{n}(\sigma_i - \sigma_{i-1})(\varepsilon_i - \varepsilon_{i-1})\right) \quad (4)$$

Hysteresis energy variation in a composite material is considerably more complex than that in a metal. To the inventors' knowledge, there have been no prior reports relating the fatigue properties of a composite material to the hysteresis energy.

Natarajan, V., GangaRao, H. V. S., Shekar, V., 2005. Fatigue response of fabric-reinforced polymeric composites. Journal of Composite Materials 39, 1541-1559 disclose a study in which three glass fabric FRP composite material coupons and systems were tested at constant low amplitude fatigue loading. Experimental results suggested that for a given FRP material and load configuration, the energy loss per cycle due to fatigue damage was linear from about 10-90% of the fatigue life of the FRP composite material. The energy loss per cycle was reported to be a characteristic value of the constituent materials, and to vary with the induced fatigue strain levels by a power law. Based on the experimental results, the authors proposed a fatigue life prediction model to predict the useful life of FRP composites, with internal strain energy as the damage metric.

Shokrieh, M. M., Taheri-Behrooz, F., 2006. A unified fatigue life model based on energy method. Composite Structures 75, 444-450 disclose a fatigue life model based on the energy method, developed for unidirectional polymer composite laminates subjected to constant amplitude, tension-tension or compression-compression fatigue loading. The fatigue model was based on a static failure criterion, and was normalized to static strength in the fiber, matrix and shear directions. The model was said to predict fatigue life for unidirectional composite laminates over the range of positive stress ratios in various fiber orientation. The results of the model were reported to agree well with experimental data for carbon/epoxy and E-glass/epoxy unidirectional plies.

Varvani-Farahani, A., Haftchenari, H., Panbechi, M., 2007. An energy-based fatigue damage parameter for off-axis unidirectional FRP composites. Composite Structures 79, 381-389 discloses a model using an energy-based fatigue damage parameter to assess the fatigue damage of unidirectional glass-reinforced plastic (GRP) and carbon-fiber reinforced plastic (CFRP) composites. The proposed parameter was based on the physics and the mechanism of fatigue cracking within three damage regions: matrix (I), fiber-matrix interface (II), and fiber (III) as the number of cycles progressed. The parameter involved the shear and normal energies calculated from stress and strain components acting on these regions. In region I the damage initiated as microcracks within the matrix. For region II, the damage progressed along the matrix-fiber interface, leading to fiber fracture in region III. The fatigue damage model was said to successfully correlate the fatigue lives of unidirectional GRP and CFRP composites at various off-axis angles and stress ratios.

Giancane, S., Panella, F. W., and Dattoma, V. 2010. Characterization of fatigue damage in long fiber epoxy composite laminates. International Journal of Fatigue, 32, 46-53 disclosed a study of damage characterization of a GFRC laminate. Forty fatigue tests were executed and S-N curves traced. Two parameters were chosen to monitor damage evolution during each test: stiffness and dissipated energy per cycle. Three zones were observed in graphs of processed. The authors suggested that the most important structural transformations occurred only in the final part of life. A method for predicting the remaining life in a GFRC was proposed.

P. Reis et al., 2010. Fatigue Damage Characterization by NDT in Polypropylene/Glass Fibre Composites. Appl. Compos. Mater. 2011, 18, 409-419 discloses the results of a study on a glass-fiber-reinforced polypropylene composite in which the fatigue damage was investigated in terms of residual stiffness and temperature rise. Thermographic and acoustic emission techniques were used to aid the interpretation of the fatigue damage mechanisms. Different laminates were tested. For one series, all the layers had one of the two fiber directions oriented with the axis of the plate. For the other two series the layer distribution was obtained with differing laminate orientations with respect to the axis of the sheet. The authors concluded that the residual stiffness and temperature rise could be used to predict final failure of a structure or component. Thermographic techniques were said to allow prediction of the site where failure would occur.

L. Toubal et al., 2006. Damage evolution and infrared thermography in woven composite laminates under fatigue loading. International Journal of Fatigue 28, 1867-1872 discloses an analytical model based on cumulative damage for predicting the damage evolution in composite materials. The model was compared with experimental data from a carbon/epoxy composite fatigued under tension-tension load. Fatigue tests of were monitored with an infrared thermography system. By analyzing the temperature of the external surface during the application of cyclic loading, it was said to be possible to evaluate damage evolution. The model was said to agree well with experimental data, and to be useful for predicting the evolution of damage in composites.

It is substantially easier to model and monitor fatigue and failure in a single-phase material, such as a metal, than in a multi-phase material, such as a composite. Results obtained in the former cannot in general be extrapolated to the latter.

We have previously reported that for two metals, Al 6061-T6 and SS 304, by tallying the entropy production up to the fracture point, one arrives at a unique material property—a so-called fracture fatigue entropy (FFE)—that is independent of geometry, load, and frequency. A necessary and sufficient condition for the metal to fracture due to cyclic loading is that its accumulated production of entropy should reach a certain level. See Naderi M, Amiri M, Khonsari M M. On the thermodynamic entropy of fatigue fracture. Proc. Roy. Soc. A. 2010; 466:423-438. See also co-pending patent application Ser. No. 12/898,100, the complete disclosure of which is incorporated by reference.

However, methods that may be successful in predicting the failure of metals cannot, in general, be successfully extrapolated to predicting the failure of composites. While metals are typically homogeneous and isotropic, most composites are neither homogeneous nor isotropic. The behaviors of damage stages and entropy accumulation are more complex in nonhomogeneous materials such as composites. Instead of a continuum damage model, which provides a good description of the development and growth of microcracks and macrocracks in many metals, in a composite material damage increases in a more complex manner, and sometimes in a sudden manner, due to matrix cracking, fiber/matrix delamination, breaking of fibers at weak interfaces, and other processes that do not have direct analogs in a single, homogeneous metal phase. In a composite there is typically a first stage that is characterized by low losses from strain energy, followed by a second stage in which damage gradually accumulates, and then a third and final phase in which there is a rapid increase in damage up to failure as the stronger fibers begin to break. Due to complexities such as these, it has been more difficult to model damage and failure in composites than in metals. Models that may work well for metals would not, in general, be expected to be successful in nonhomogeneous materials such as composites.

Many previous models of fatigue failure for composites have been based on the assumption that cycles of stress have constant amplitude, or other simplified loading conditions. There remains an unfilled need for a general method for monitoring and predicting fatigue failure for composite materials under more variable, "real world" loading conditions.

SUMMARY OF THE INVENTION

We have discovered that fatigue failure in composite materials can be successfully modeled and predicted by monitoring irreversible gains in their entropy. Permanent degradations in composites are marked by irreversible processes that are characterized by increases in entropy. Entropy is a measure of disorder. By measuring changes in entropy, one can model and predict the deterioration and failure of composites. The novel technique may be used to predict the deterioration and failure of composites under essentially any type of loading—constant, variable, bending, torsion, tension, compression, etc.

We describe here both the theory underlying the invention, and prototype experiments that we have conducted to confirm the efficacy of the invention in practice. For example, we have quantified the entropy gain both in displacement-control bending fatigue and in load-controlled tension-tension fatigue for a composite laminate (Epoxy/Glass: G10/FR4) that was subjected to constant or variable amplitude loading (high-to-low or low-to-high load), to various load ratios, to loading using different fiber orientations, and to different driving frequencies. In each case, the measured entropy gains correlated well with observations of failure of the composite materials.

BRIEF DESCRIPTION OF THE DRAWINGS

FIGS. 12(a)-(e) depict results from an extensive set of fatigue tests conducted on a Glass/Epoxy laminate at different stress ratios and load angles at a frequency of 10 Hz. FIG. 12(a) depicts the stress life approach. FIG. 12(b) depicts the elastic strain energy method. FIG. 12(c) depicts the cyclic hysteresis energy method. FIG. 12(d) depicts the accumulated fracture energy method. FIG. 12(e) depicts the fracture fatigue entropy model.

MODES FOR CARRYING OUT THE INVENTION

Figure 1A:
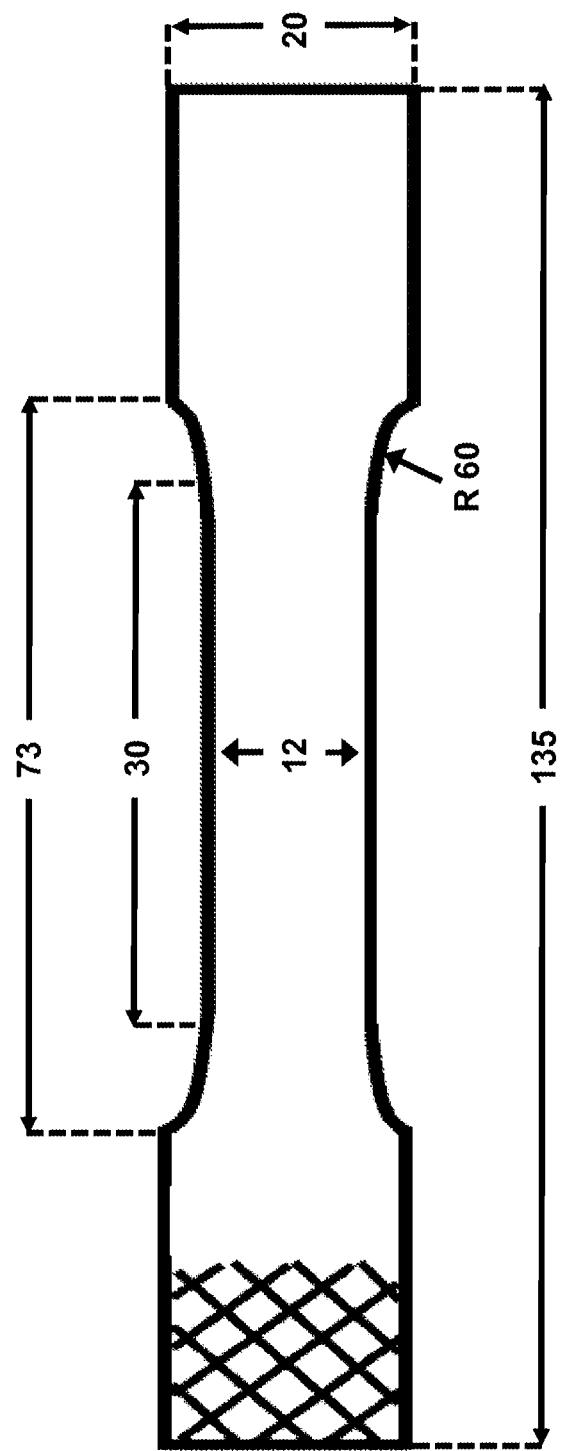
FIG. 1(a) presents schematically a diagram of the experimental setup used for a tension-tension fatigue test using a servohydraulic single actuator.

The first law of thermodynamics states that the internal energy within an arbitrary control volume changes only as energy flows into (or out of) that volume:

$$\frac{dE}{dt} = \frac{dQ}{dt} + \frac{dW}{dt} \quad (5)$$

where E is total energy, t denotes time, Q and W are heat flow and work across the boundary of the control volume, respectively. (By convention, the energy added to the control volume is positive.)

For an open system, i.e. one that can exchange heat with its environment, the total change of entropy ($d_tS$) consists of two terms: the entropy flow into or out of the system, $d_eS$, and the entropy produced within the system, $d_iS$:

$$\frac{d_tS}{dt} = \frac{d_iS}{dt} + \frac{d_eS}{dt} \quad (6)$$

The entropy exchanged with the surroundings, $d_eS$, can be either positive or negative. By the second law of thermodynamics (Clausius-Duhem inequality) the entropy generated within the system must be non-negative, i.e., $$d_iS \geq 0 \quad (7)$$

Equations (5) and (6) can be rewritten as:

$$\rho \frac{du}{dt} = -\nabla \cdot J^q + w \quad (8a)$$

$$u = \rho c \frac{\partial T}{\partial t} + e_d \quad (8b)$$

$$\rho \dot{s} = -\nabla \cdot J^s \dot{\gamma} \quad (9)$$

where ρ is the density, u denotes specific internal energy, $J^q$ is heat flux across the boundary, and w is the rate of volumetric work of permanent deformation. The parameter s represents the total entropy per unit mass. $J^s$ is the entropy flow and γ denotes the volumetric entropy production. The specific heat is denoted c, and $e_d$ represents the damage energy.

Using the definition of Helmholtz free energy, $\Psi = u - T \cdot s$, the energy balance and the entropy production Eqs. (8a) and (9) can be rewritten:

$$\rho(\dot{\Psi} + \dot{T}s + T\dot{s}) = -\nabla \cdot J^q + w \tag{10}$$

$$\dot{\gamma} = \frac{w}{T} - \frac{\rho(\dot{\Psi} + \dot{T}s)}{T} - \frac{J^q \cdot \nabla T}{T^2} \geq 0 \tag{11}$$

where T denotes the temperature.

By introducing specific heat capacity, c, and using Fourier's heat conduction law ($J^q = -k\nabla T$), one can obtain the following general form of the heat conduction equation and entropy production inequality:

$$kT_{,ii} + w = \rho c \dot{T} \tag{12}$$

$$\dot{\gamma} = \frac{w}{T} + \frac{e_d}{T} + \frac{k}{T^2} T_{,i} T_{,i} \geq 0 \tag{13}$$

where k is the thermal conductivity; and $T_{,i}$ and $T_{,ii}$ are the first and second derivatives of T, respectively.

Eq. (13)—the entropy generation inequality—contains three terms: the mechanical dissipation due to permanent deformation $$\left(\dot{\gamma}_{mech} = \frac{w}{T}\right),$$

the internal evolution variable $$\left(\dot{\gamma}_d = \frac{e_d}{T}\right),$$

and the thermal dissipation due to heat conduction $$\left(\dot{\gamma}_{cond} = \frac{k}{T^2} T_{,i} T_{,i}\right).$$

The fracture fatigue entropy (FFE), $\gamma_f$, can be obtained by integrating Eq. (13) up to the time $t_f$ when failure occurs:

$$\gamma_f = \int_0^{t_f} \left(\frac{w}{T} + \frac{e_d}{T} + \frac{k}{T^2} T_{,i} T_{,i}\right) dt \tag{14}$$

An order-of-magnitude analysis leads to the conclusion that entropy generation from mechanical dissipation dominates, and that entropy generation from heat conduction is comparatively negligible. As an approximation, Eq. (14) reduces to:

$$\gamma_f = \int_0^{t_f} \left(\frac{w}{T} + \frac{e_d}{T}\right) dt \tag{15}$$

Experimental measurements of temperature and variations in strain energy variation can be used in Eq. (15) to calculate the fracture fatigue energy, FFE, for a system. The damage energy can be obtained by subtracting the energy dissipated through heat from the strain energy. Numerical values for both w and $e_d$ will usually be measured in advance for a particular material of interest. Although these values will generally vary between different composite materials, for a given material the values of w and $e_d$ are often relatively constant until near the end of the life of the material, when they can begin to deviate. The previously measured values of the parameters w and $e_d$ can be used when taking measurements and applying Equation (15) to determine γ in a particular situation.

Example 1

An order-of-magnitude analysis will show that the entropy generation from heat conduction is negligibly small compared to that from mechanical dissipation. A tension-tension fatigue test with 5 kN load amplitude, load ratio of zero, and frequency of 10 Hz is considered in this analysis. Referring to Equation 14, and considering only mechanical and thermal dissipation:

$$\dot{\gamma} \approx \frac{w}{T} + \frac{k}{T^2}\left(\frac{\Delta T}{\Delta y}\right)^2 \approx \dot{\gamma}_{mech} + \dot{\gamma}_{cond} \tag{16}$$

where ΔT represents the temperature difference between two cross-sections at a distance Δy from one another, where one of the two cross-sections is that at which failure occurs. Taking Δy=1.2 mm, and using actual measurements from our laboratory, Equation (16) was used to calculate the effects of mechanical dissipation and thermal dissipation on entropy production. Table 1 summarizes the results of this scale analysis. Entropy from mechanical dissipation was dominant, and entropy from heat conduction was negligible. Thus Equation (16) reduces to $$\dot{\gamma} \approx \frac{w}{T} \approx \dot{\gamma}_{mech} \tag{17}$$

TABLE 1

Order of magnitude calculations from tension-tension fatigue test measurements

| % of total life ($N_f$) | ΔT (° C.) | $T_I$ (° C.) | w (KJ m$^{-3}$) | $\dot{\gamma}_{mech} / \dot{\gamma}_{cond}$ |
|---|---|---|---|---|
| 5 | 0.1 | 22.4 | 42.4 | 66782 |
| 60 | 0.3 | 47.7 | 54 | 10253 |
| 90 | 3 | 62.5 | 75 | 150 |

Example 2

The material studied in a prototype example was Epoxy/Glass G10/FR4, a laminate composite of a continuous filament glass cloth and an epoxy resin binder. This composite has high tensile and flexural strength (see Table 2), and is used in a variety of applications such as electrical equipment, aerospace structures, and rocket structural components. Specimens were prepared with the glass fibers oriented lengthwise (at) 0°, crosswise (90°), and at several off-axis directions: 15°, 30°, 45°, 60°, and 80°.

TABLE 2

Mechanical properties of G10/FR4

| Tensile Strength (MPa) | | Flexural Strength (MPa) | | Elastic Modulus in Flexure (GPa) | |
|---|---|---|---|---|---|
| Lengthwise | Crosswise | Lengthwise | Crosswise | Lengthwise | Crosswise |
| 275 | 240 | 380 | 310 | 18 | 15 |

Example 3

FIG. 1(a) presents schematically a diagram of the experimental setup used for a tension-tension fatigue test using an MTS 810 servohydraulic single actuator. Unless context indicates otherwise, the numerals in FIGS. 1(a) and 1(b) denote dimensions in millimeters. Sinusoidal fatigue loads were controlled with Multipurpose TestWare (MPT) software. Loads were applied at a frequency between 5 and 15 Hz, and a load ratio R (the ratio of the minimum load to the maximum load) between 0 and 0.1. Constant and variable loads were applied, both on-axis (0 and 90°), and off-axis (15, 30, 45, 60 and 80°) to the orientation of the glass fibers. Variable loads were applied either high-to-low or low-to-high.

Example 4

Figure 1B:
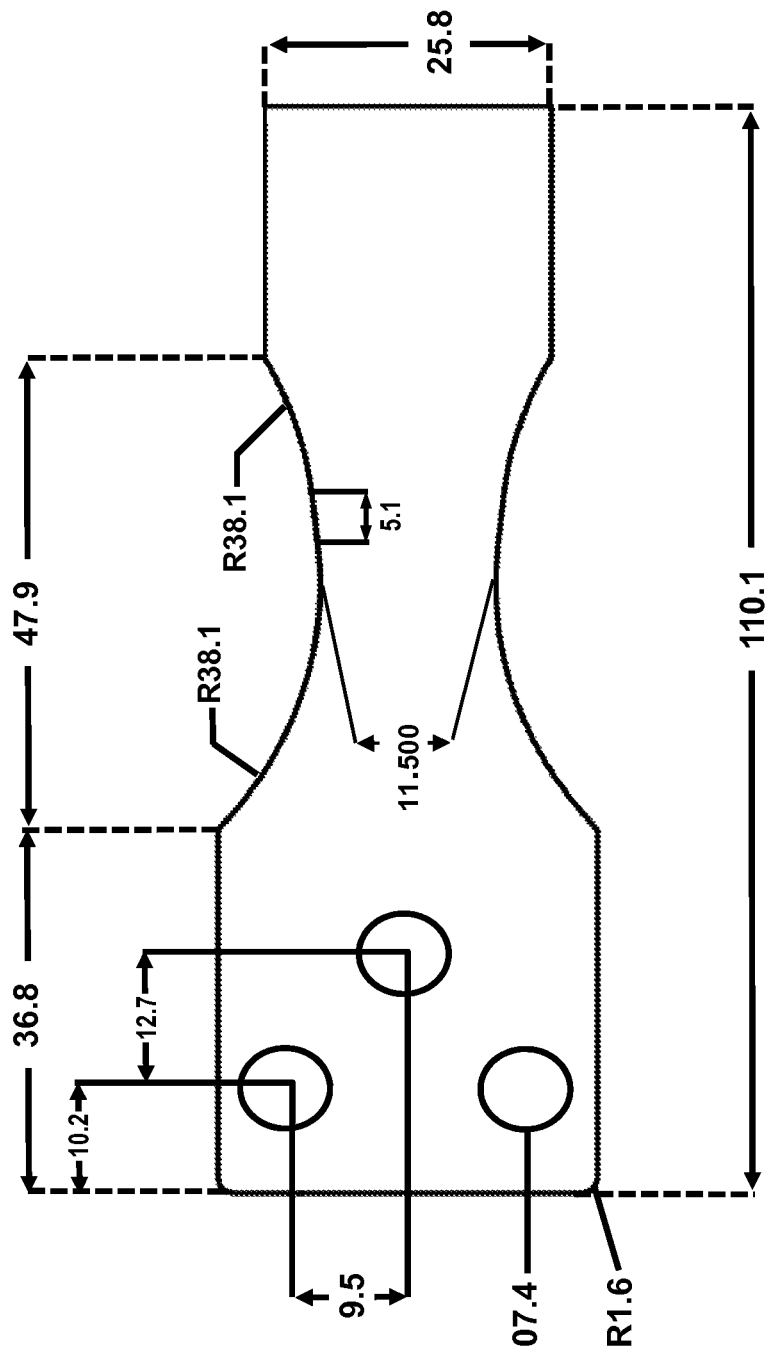
FIG. 1(b) depicts schematically a specimen used for a bending fatigue test.

FIG. 1(b) depicts schematically a specimen used for a bending fatigue test. A fully reversed bending fatigue testing apparatus was used—a compact, bench-mounted unit with a variable-speed motor, a variable-throw crank connected to a reciprocating platen, a failure cut-off circuit in a control box, and a cycle counter. The variable-throw crank was continuously adjustable from 0 to 50.8 mm to provide different stress amplitudes.

Example 5

For the tension-tension fatigue tests we tested 62 different constant loads and 16 variable loads (both high-to-low and low-to-high), for two different specimen thicknesses (3 and 4.85 mm), over a load amplitude range between 2 and 10 kN. For the bending fatigue tests, 16 constant amplitude loads were tested with 3 mm-thick specimens. Test conditions are summarized in Table 3.

TABLE 3

Fatigue Test conditions

| Fatigue Test | Frequency (Hz) | Specimen Thickness (mm) | Number of Tests | | Load Amplitude |
|---|---|---|---|---|---|
| | | | Constant Load | Variable Load | |
| Tension-Tension | 5, 10, 15 | 3, 4.85 | 62 | 10 | 2-10 (kN) |
| Bending | 10 | 3 | 16 | — | 20-50 (mm) |

The instrumentation included high-speed, high-resolution infrared (IR) thermography to record the temperature of the specimen during the course of the experiment. The IR camera was a MIKRON M7500 with temperature range from 0° C. to 500° C., 320×240 pixel resolution, ±2% accuracy, 0.08° C. sensitivity/NETD (noise equivalent temperature difference) at 30° C., and an image update rate of 7.5 Hz. Before fatigue testing, the surface of the specimen was covered with black paint to enhance the thermal emissivity of the specimen surface.

Hysteresis Energy

Example 6

Figure 2:
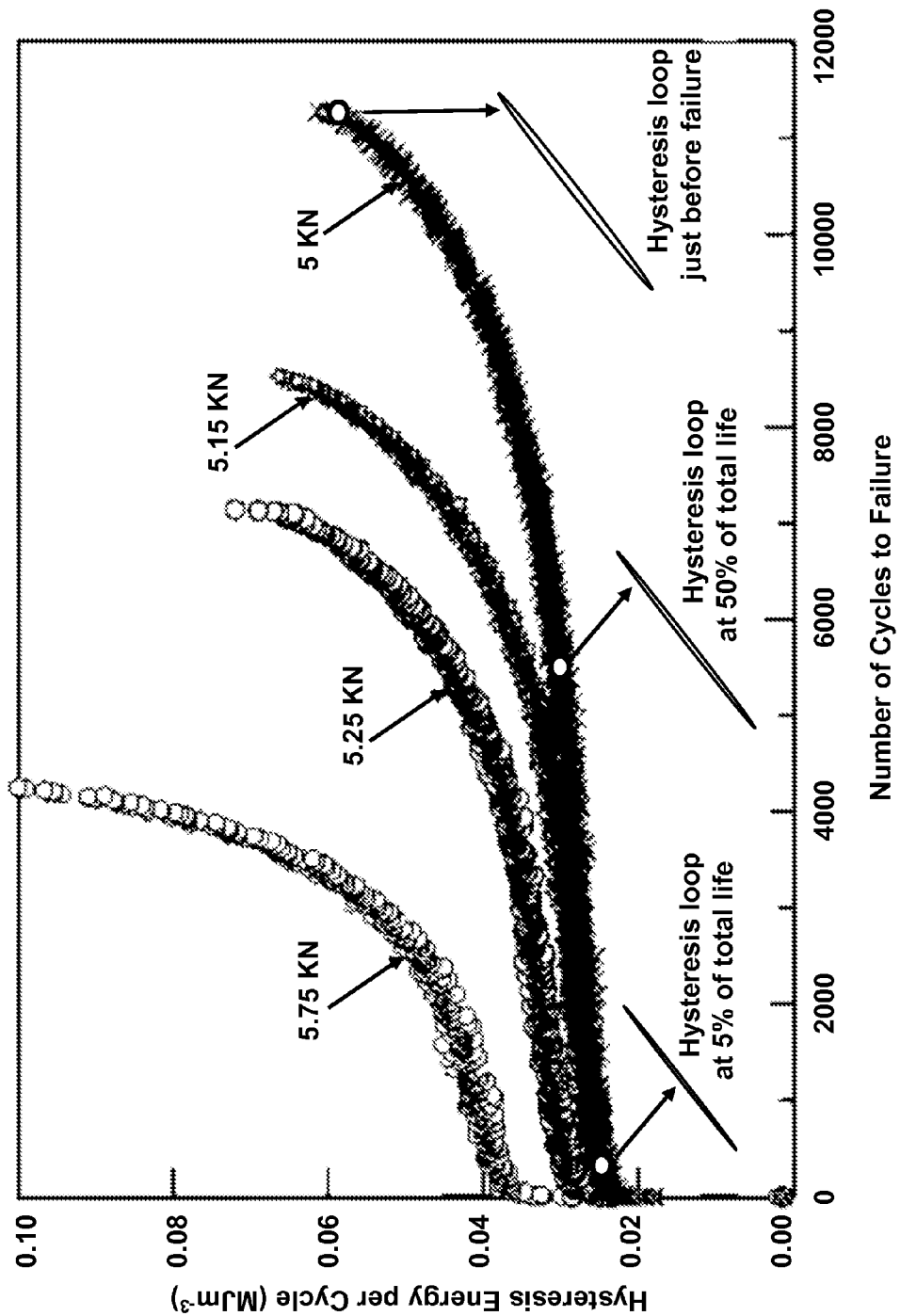
FIG. 2 depicts the increase in the area of the hysteresis loop—the so-called strain energy—in a composite laminate measured during a series of tension-tension fatigue tests.

FIG. 2 depicts the increase in the area of the hysteresis loop—the so-called strain energy—in the G10/FR4 composite laminate measured during a series of tension-tension fatigue tests (R=0) at a frequency of 10 Hz. The hysteresis area for each cycle was obtained with a MATLAB™ program based on experimental load and displacement data for the loading and unloading paths. Typical experimentally-determined hysteresis curves at 5% of total life, 50% of total life, and just before failure are also shown in FIG. 2, each for a 5 kN load amplitude. Similar to the behavior of the temperature (as discussed below), the behavior of the strain energy underwent three stages. The first stage occurred during about the first 15 to 20% of total life, and was characterized by low losses from strain energy. During the second stage, which lasted about 70-75% of total life, there was a slow and gradual increase in strain energy, accompanied by matrix cracking and matrix/fiber interfacial delamination. The third and final stage prior to failure was characterized by higher strain energy release and fiber breakage.

Temperature and Entropy Evolution

Example 7

Figure 3:
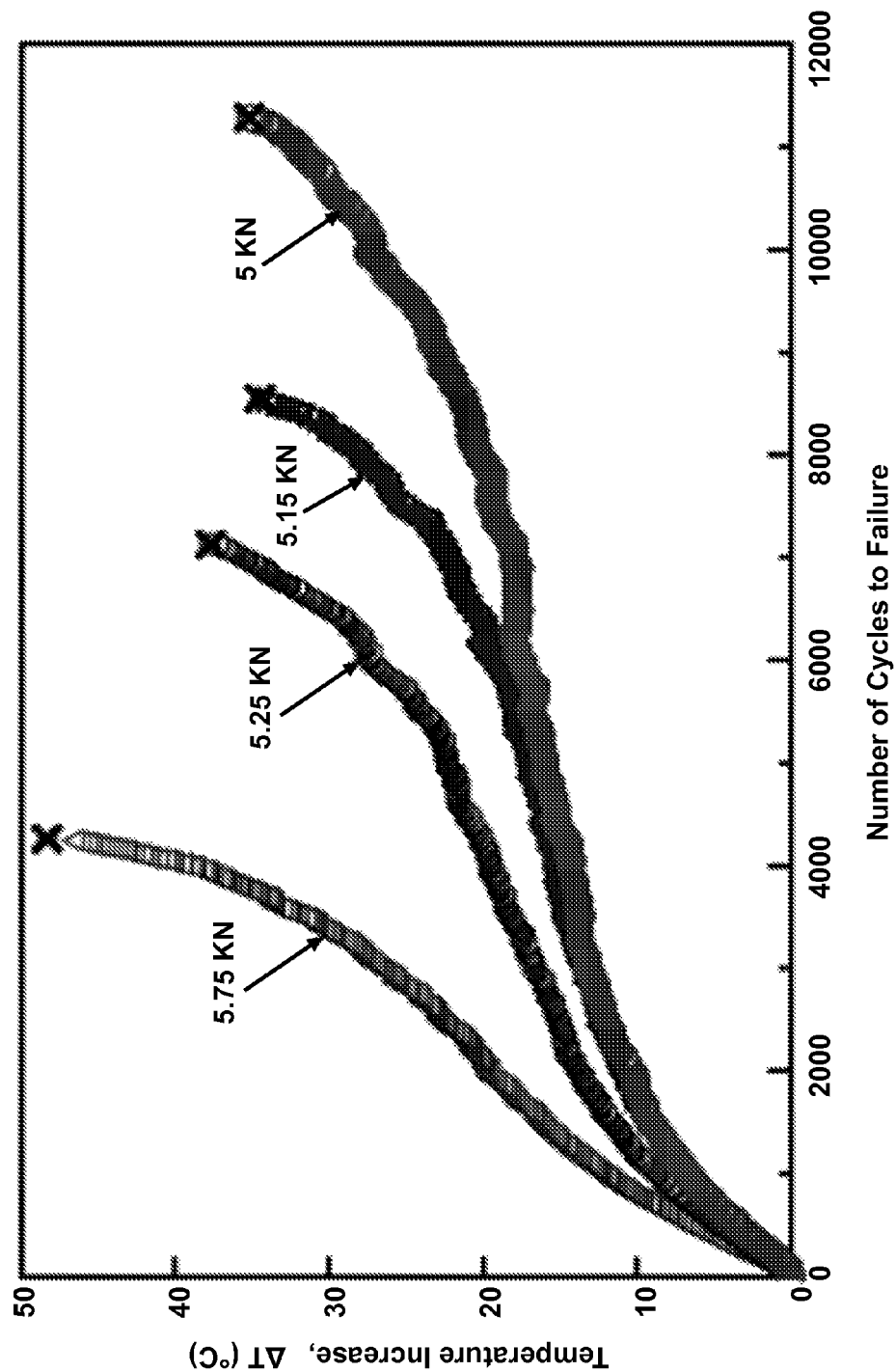
FIG. 3 depicts surface temperature in a composite laminate versus the number of cycles, up to the point of failure, for a series of tension-tension fatigue tests for various load amplitudes.

FIG. 3 depicts the surface temperature that was recorded with an IR camera, plotted versus the number of cycles to the point of failure for a series of tension-tension fatigue tests at various load amplitudes with a frequency of 10 Hz and R=0. The temperatures shown in FIG. 3 were those measured at the cross section where failure ultimately occurred. While it is not necessary to know in advance the precise location where failure will occur, an experienced operator typically knows where failure is most likely. For example in a bending specimen, failure will typically occur near the clamped end. In tension-compression, failure is typically near the middle of the specimen's gage section. FIG. 3 shows a relatively steep temperature increase initially, followed by a slow, nearly linear rise. Finally, a steeper increase in temperature occurred just before the specimen failed.

Figure 4A:
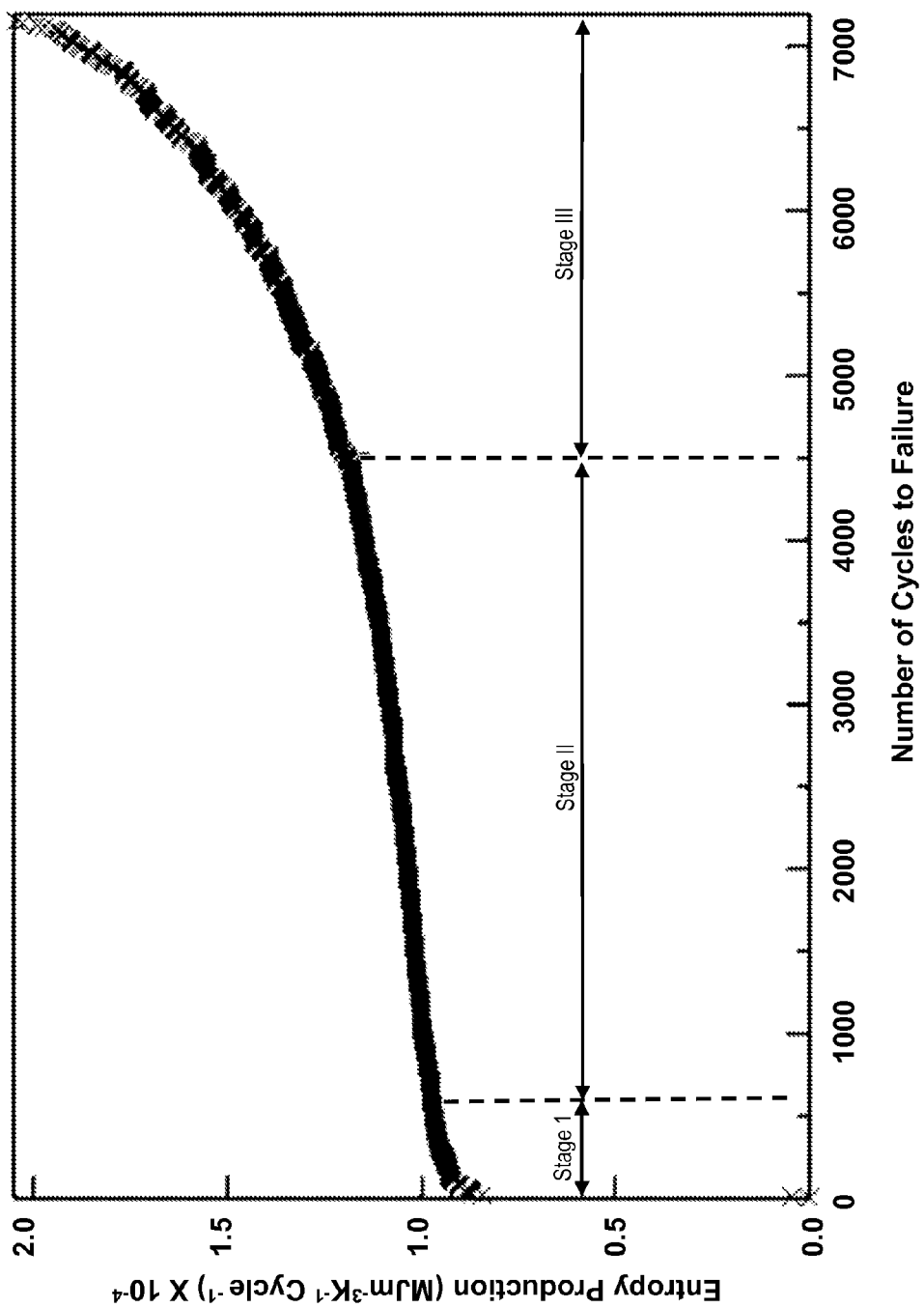
FIG. 4(a) depicts calculated entropy production in a composite laminate in a series of tension-tension fatigue tests.
Figure 4B:
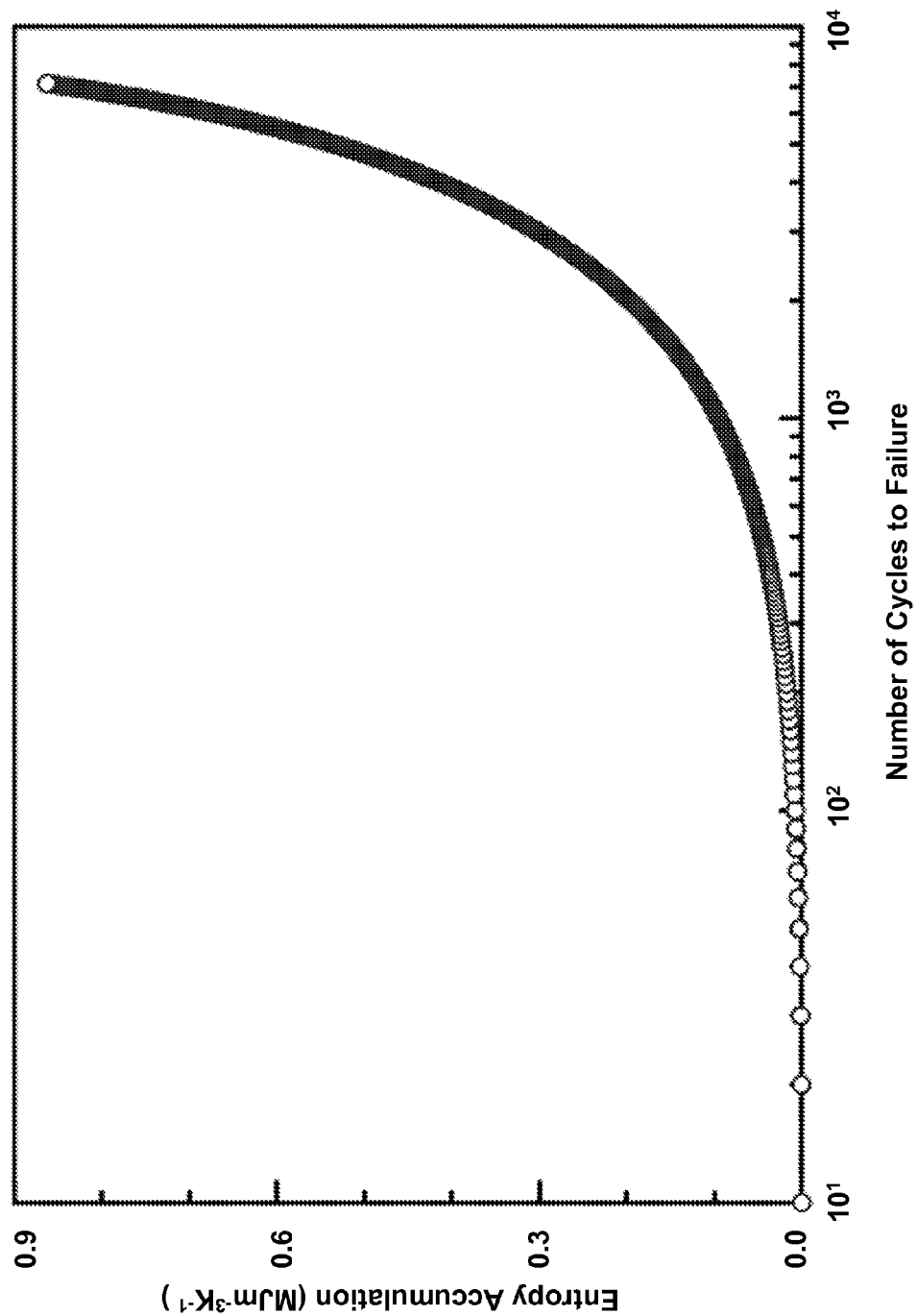
FIG. 4(b) depicts calculated entropy accumulation in a composite laminate in a series of tension-tension fatigue tests.

The entropy production rate and entropy accumulation were calculated from Eqs. (13) and (14) for the tension-tension fatigue test with a 5.25 kN load amplitude at a frequency of 10 Hz. Entropy production is depicted in FIG. 4(a), and entropy accumulation is depicted in FIG. 4(b). Note that in FIG. 4(a) both axes are linear, while FIG. 4(b) is a semi-log plot. FIG. 4(a) reveals that entropy production proceeded in three stages: an initial rise (first stage), up to about 500 cycles; then a slow and steady increase (second stage), from about 500 to about 4500 cycles; and finally a strong increase until failure (third stage), from about 4500 cycles to about 7200 cycles. During the first stage, entropy accumulated primarily as a result of the energy released at the tips of micro-cracks in multiple locations in the matrix, debonding at weak interfaces between fibers and matrix, and breakage of some fibers having low strength. We noted that the changes in the degradation mode affected the heat dissipation rate, and consequently the rate of entropy production. During the comparatively small number of cycles in the first phase, relatively low levels of entropy accumulated. Once crack density in the matrix became more-or-less saturated, the trend of further degradation changed. Existing cracks then grow towards the fiber/matrix interface. At the interface the cracks do not cross the high-strength fiber, and instead can progress in either or both of two directions: Some cracks move along the fiber, and some run around the fiber. These cracks slowly propagate. At this stage, entropy was produced at a lower rate due to slower heat generation and a slower damage process. However, entropy accumulation was more pronounced than in the first stage because the second stage occupied a longer fraction of total lifetime prior to failure (around 55% of total life). At the beginning of the third stage, the predominant form of degradation changed from matrix cracking to fiber breakage. Entropy production and accumulation then rose rapidly after a comparatively small number of cycles until failure occurred from fiber breakage.

Tension-Tension Fatigue Measurements

Example 8

Figure 5A:
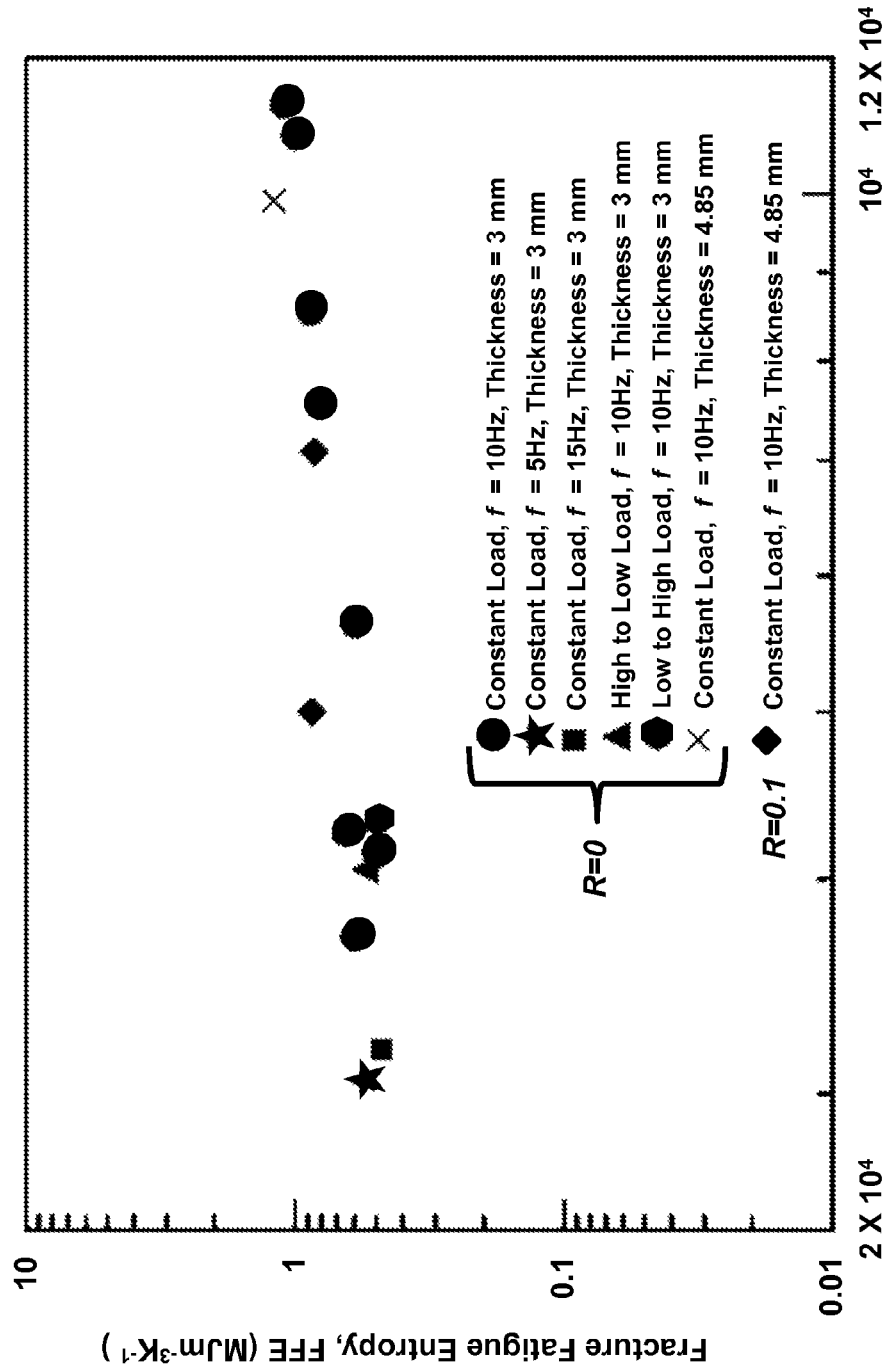
FIG. 5(a) depicts fracture fatigue entropy in the crosswise (90°) direction.
Figure 5B:
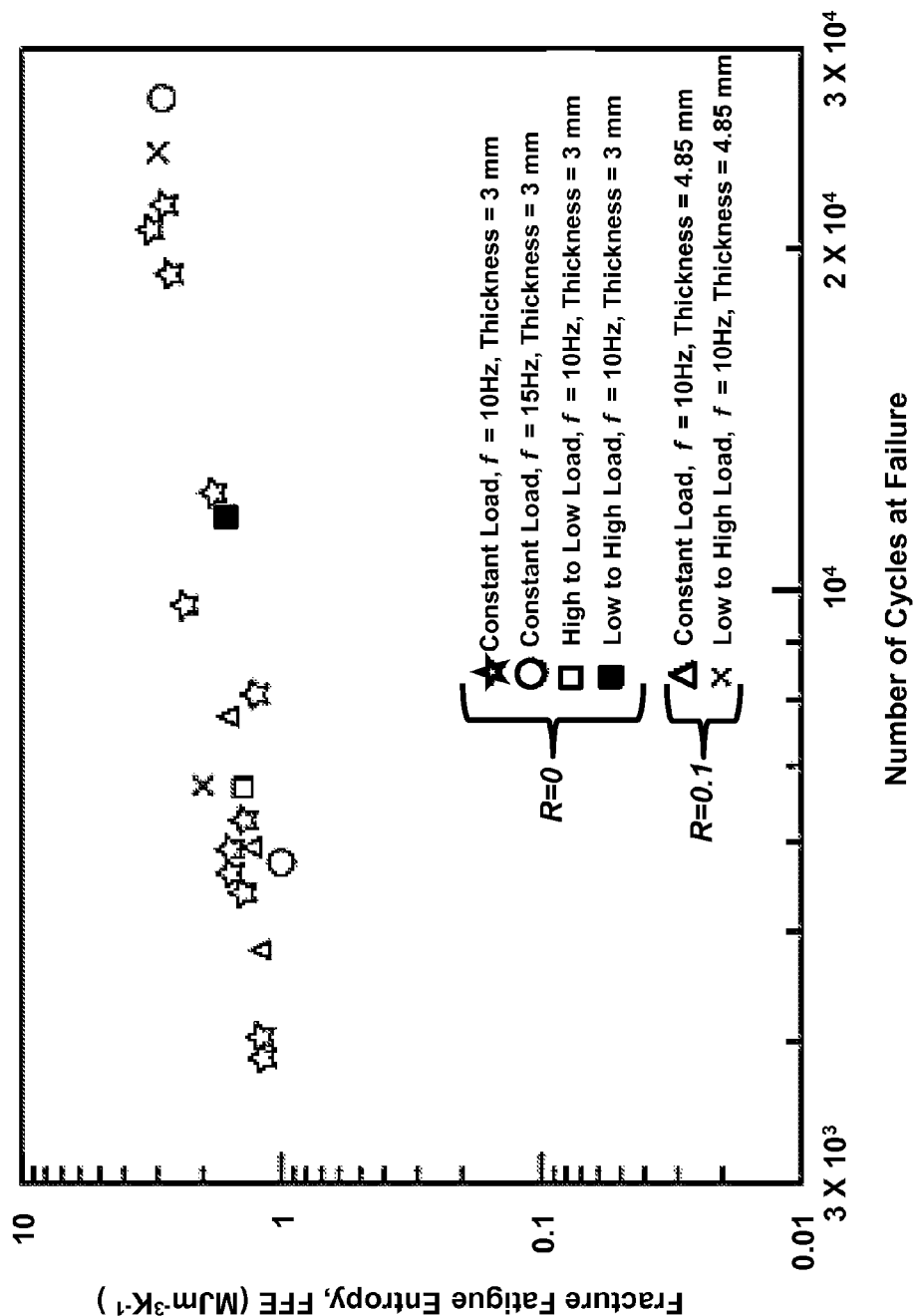
FIG. 5(b) depicts fracture fatigue entropy in the lengthwise (0°) direction.
Figure 5C:
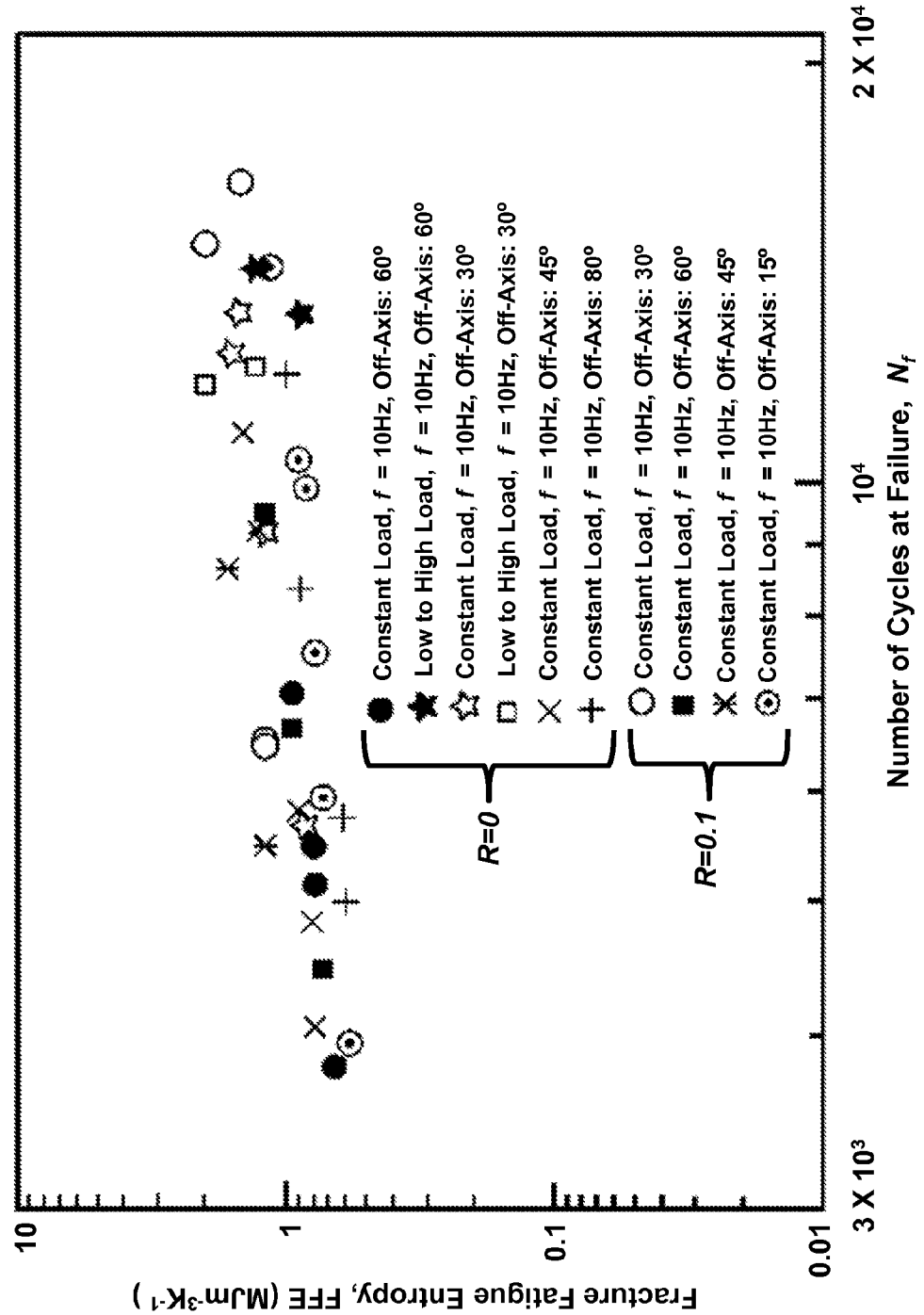
FIG. 5(c) depicts off-axis fracture fatigue entropy at angles of 15°, 30°, 45°, 60°, and 80°.

FIGS. 5(a)-5(c) depict measured values of FFE versus number of cycles to failure in several tension-tension fatigue tests. FIG. 5(a) depicts fracture fatigue entropy in the crosswise (90°) direction. Constant loads were 4.9 to 9.5 kN, and variable loads were 5.15 to 6 kN and 6 to 5.15 kN. FIG. 5(b) depicts fracture fatigue entropy in the lengthwise (0°) direction. Constant loads were 5 to 13.5 kN, and variable loads were 5.7 to 6 kN and 6 to 5.7 kN. Fracture fatigue entropies ranged from 1 to 3 MJm$^{-3}$K$^{-1}$. FIG. 5(c) depicts off-axis fracture fatigue entropy at angles of 15°, 30°, 45°, 60°, and 80°. Loads were 2.5 kN to 5 kN.

The results showed that FFE at the fracture point for G10/FR4 was approximately 0.8 MJm$^{-3}$K$^{-1}$ at an angle of 90°, about 1.5 MJm$^3$K$^{-1}$ at an angle of 0°, and about 1 MJm$^{-3}$K$^{-1}$ for each of the off-axis angles (15, 30, 45, 60, and 80°). The measured values of FFE were largely independent of frequency and load, and depended only weakly upon fiber orientation. The measured values of FFE were also largely independent of any loading sequence effect under variable loading conditions (e.g., high-to-low or low-to-high load).

Figure 5D:
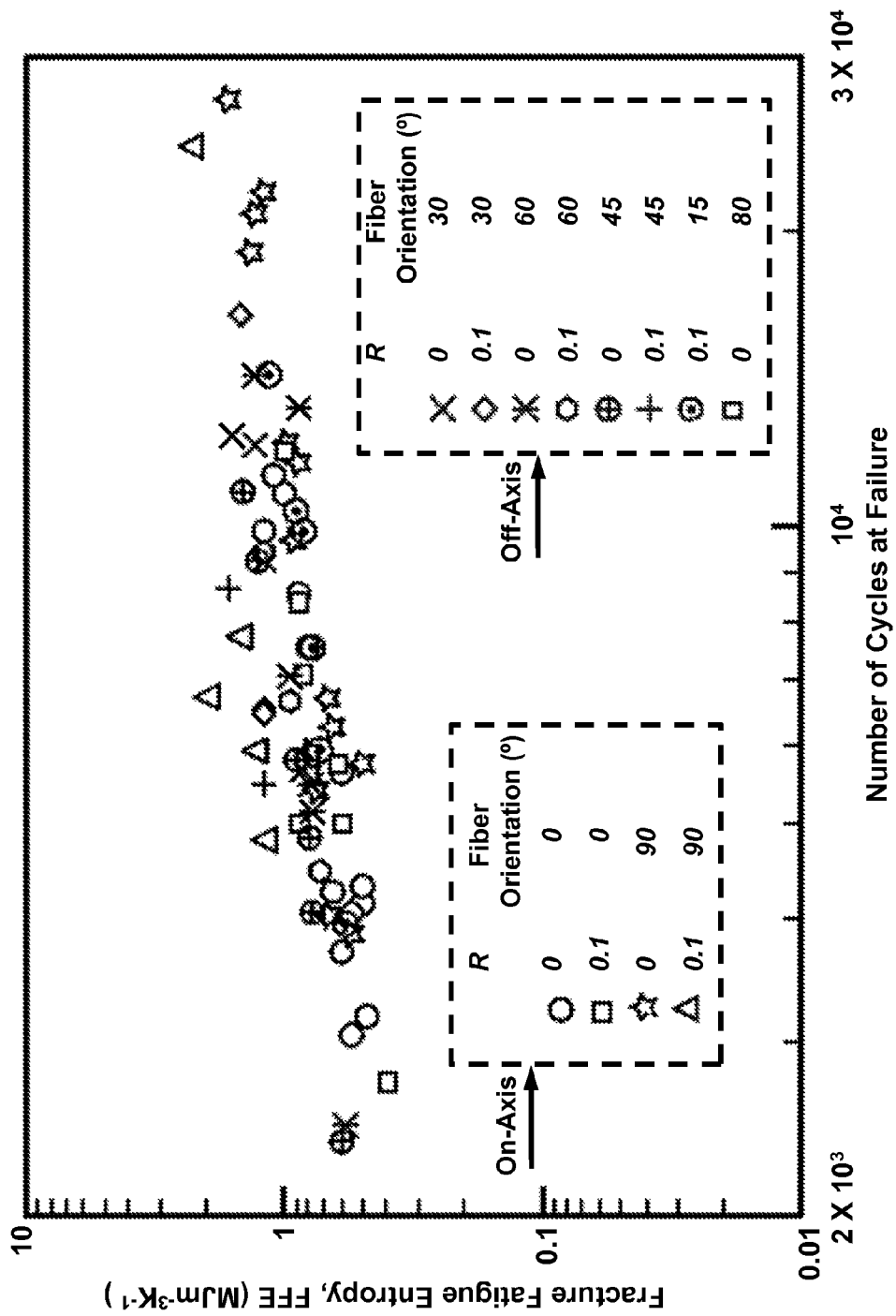
FIG. 5(d) combines the fracture fatigue entropy data from FIGS. 5(a)-5(c) into a single plot.

FIG. 5(d) combines the fracture fatigue entropy data from FIGS. 5(a)-5(c) into a single plot. In FIG. 5(d), all the entropy accumulation measurements fell within a single, relatively narrow band, as compared to measurements using energy- or stress-based models. The measured FFE values were largely independent of loading sequence, frequency, load ratio, and fiber orientation.

Bending Fatigue

Example 9

Fully-reversed bending fatigue tests were carried out at fiber orientations of 0 and 90° at a frequency of 10 Hz. The bending tests were performed with a Fatigue Dynamics compact, bench-mounted unit with a variable speed motor, a variable throw crank connected to a reciprocating platen, a failure cut-off circuit in a control box, and a cycle counter. In these tests, the dissipated strain energy—which was utilized to determine the entropy accumulation—was estimated using the procedure described in Meneghetti G. Analysis of the fatigue strength of a stainless steel based on the energy dissipation. Int J. Fatigue. 2007; 29(1):81-94. Briefly, the cooling rate was measured after a sudden interruption of the fatigue test. The energy balance is:

$$w = h + \rho c \frac{\partial T}{\partial t} + e_d \qquad (18)$$

where w is the input mechanical energy. The parameter h denotes the rate of dissipation of thermal energy in a unit volume due to the combined effects of conduction, convection, and radiation. The remaining two terms on the right hand side account for the rate of variation of internal energy: the first term depends on the temperature variation of the material; and the second term, $e_d$, is the time rate of variation of the so-called stored energy of cold work, which is that part of the input mechanical energy that goes into creating new surfaces, internal cracks, and changes in material micro-structures.

Figure 6:
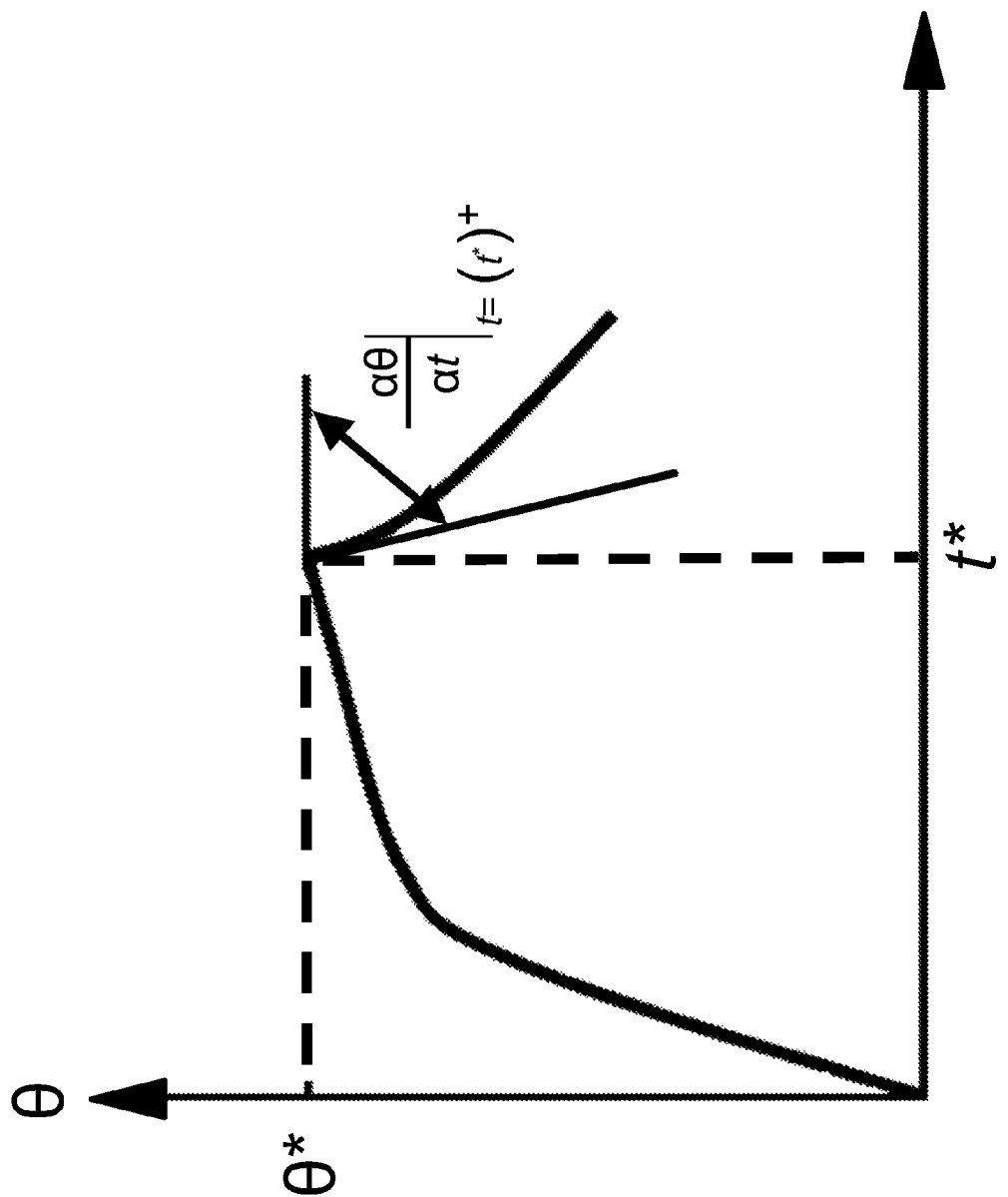
FIG. 6 depicts the temperature of the composite laminate when a fatigue test was suddenly stopped.

As shown schematically in FIG. 6, the fatigue test was suddenly stopped at a time t* when the mechanical input power and thus the time rate of variation of cold work, $e_d$ in Eq. (18), had both dropped essentially to zero. At time t* the surface temperature was T*. Just after $$t=(t^*)^+ \qquad \text{Eq. (18)}$$

can be written as:

$$-h = \rho c \frac{\partial T}{\partial t}\bigg|_{t=(t^*)^+} \qquad (19)$$

Measuring the rate of temperature change as a function of time during the cooling period after the fatigue test had ended supplied the data for the right side of Eq. (19). The thermal energy per unit volume per cycle, q, is:

$$q = \frac{h}{f} \qquad (20)$$

where f is the frequency of the test.

Validation of the Hysteresis Energy Estimation

Example 10

To support the validity of our model for determining hysteresis energy in a tension-tension fatigue test, we compared our results to the hysteresis energy as measured directly by a Material Testing Systems (MTS) 810 servo-hydraulic actuator instrument.

Figure 7:
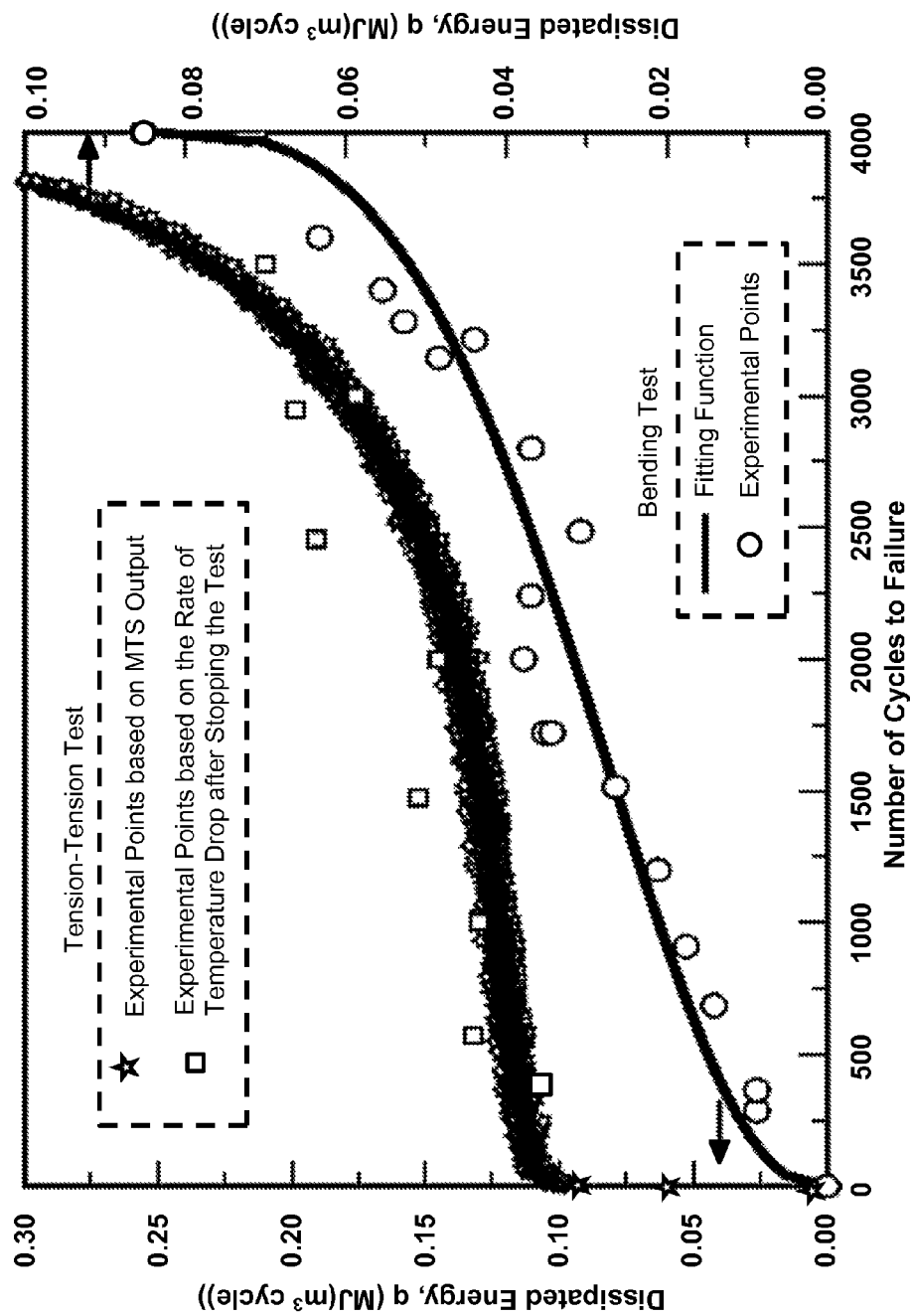
FIG. 7 depicts the strain energy evolution and the cyclic dissipated energy for a tension-tension fatigue test.

The upper curve in FIG. 7 depicts the strain energy evolution for a tension-tension fatigue test at a frequency of 10 Hz, R=0, and 5.75 kN load amplitude. The curve-fitting toolbox of MATLAB™ was used to generate the cooling curves from which the rate of drop in temperature, $$\frac{\partial T}{\partial t},$$

was calculated and then used in Eqns. (18) and (19) to evaluate the cyclic strain energy. The results showed that the energy dissipation we determined by abruptly stopping the fatigue test was in good agreement with the MTS measurements. Because the bending fatigue machine did not have the capability to obtain data for hysteresis loop and stress, this method was applied for bending tests to determine the strain energy per cycle for different series of tests.

Hysteresis Energy in Bending Fatigue

Example 11

The lower curve in FIG. 7 depicts measurements of cyclic dissipated energy that were obtained by stopping the fatigue test, for a bending fatigue test at a frequency of 10 Hz and a displacement amplitude of 38.1 mm.

Figure 8:
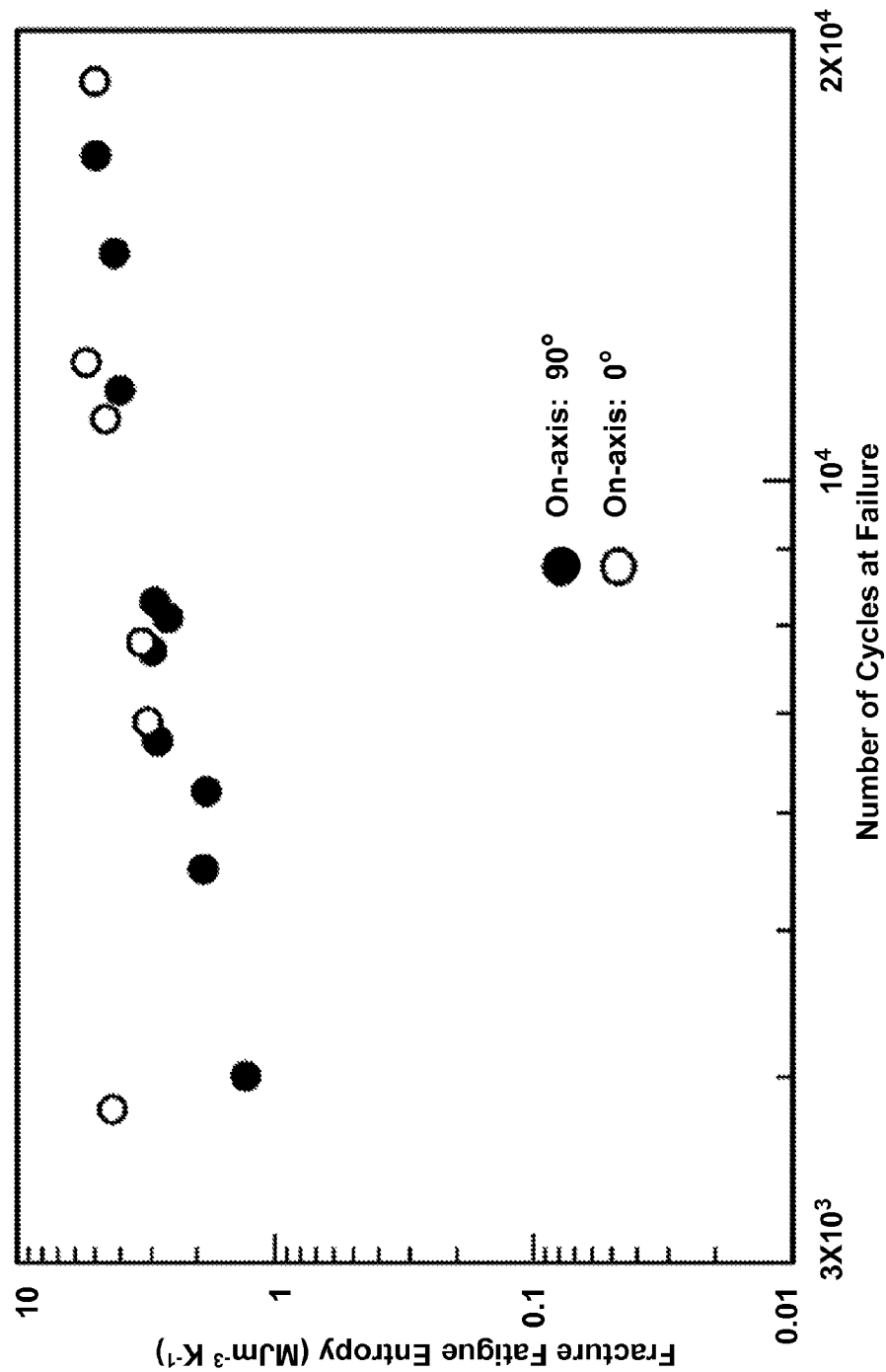
FIG. 8 depicts FFE values that were calculated from dissipated energy measurements for different series of bending fatigue tests for two different fiber axis directions, for different loads (30-50 mm displacement amplitudes).

FIG. 8 depicts FEE values that were calculated from the dissipated energy measurements for different series of bending fatigue tests for two different fiber axis directions, for different loads (30-50 mm displacement amplitudes), at a frequency of 10 Hz. The vertical axis shows the accumulated entropy at fracture, $\gamma_f$, and the horizontal axis shows the number of cycles to failure. The observed values fell within relatively narrow upper and lower limits for the FFE parameter, independent of both load amplitude and fiber orientation. In particular, the FFE for a G10/FR4 composite laminate was approximately 2.5 MJm$^{-3}$K$^{-1}$ for a fiber orientation of 90°, and 3 MJm$^{-3}$K$^{-1}$ for 0°.

These results support our hypothesis that entropy at failure for Epoxy/Glass (G10/FR4) for tension-tension fatigue and bending fatigue fall within smaller upper and lower ranges at failure than measurements based on stress or energy models. In the tension-tension fatigue tests, final fracture of the glass/epoxy composite corresponded to an entropy gain of approximately 0.8 MJm$^{-3}$K$^{-1}$ at an angle of 90°, approximately 1.5 MJm$^{-3}$K$^{-1}$ for 0°, and approximately 1 MJm$^{-3}$K$^{-1}$ for each of the off-axis angles tested (15, 30, 45, 60, and 80°). In the bending fatigue tests, final fracture corresponded to an entropy gain of approximately 2.5 MJm$^{-3}$ K$^{-1}$ at 90°, and approximately 3 MJm$^{-3}$K$^{-1}$ at 0°.

There was a small apparent increase in FFE as the fatigue life increased. This apparent increase may be the result of disregarding the heat conduction term in Eq. (14). We note that accumulated entropy due to damage energy was not considered in the FFE results.

Further Studies

Nomenclature Used in these Studies

Example 12

The material studied in this series of experiments was also Glass/Epoxy (G10/FR4). This composite has high tensile and flexural strength. It is an unbalanced, woven fabric with a plain weave and an aligned configuration. It contains a continuous filament glass cloth with an epoxy resin binder that is cured as a multilayered laminate under heat and pressure to form solid shapes. A grade #10 (i.e., G10) epoxy is injected into layers of fiberglass sheets, heated, and pressed at high pressure. "FR4" refers to a fire retardant grade of G10. For example, fifteen layers of plain woven glass fabric would be stacked to make a thickness of 3 mm. Each woven layer has two unidirectional layers stacked in orthogonal directions [0°/90°]. Specimens can be prepared with different stacking sequences. For on-axis stacking, the warp or weft direction is aligned with the load direction. The warp and the weft directions are sometimes called the lengthwise (0°) and the crosswise) (90° directions, respectively. For off-axis stacking, the angle between the warp and the load direction, θ, is between 0° and 90°—viz., 15°, 30°, 45°, 60° or 80° in the examples we tested.

High-speed, high-resolution infrared (IR) thermography was used to record the temperature of the specimens as it changed over time. Tests were conducted with an MTS 810 servohydraulic single actuator. Static tests were conducted initially to measure the laminate's ultimate tensile strength and modulus of elasticity. Next, extensive experiments were performed with a sinusoidal load applied at a frequency of 10 Hz and load ratios, R, of 0 and 0.1. Finally, constant- and variable-load amplitudes (high-to-low and low-to-high) were applied in load-controlled mode.

Figure 9A:
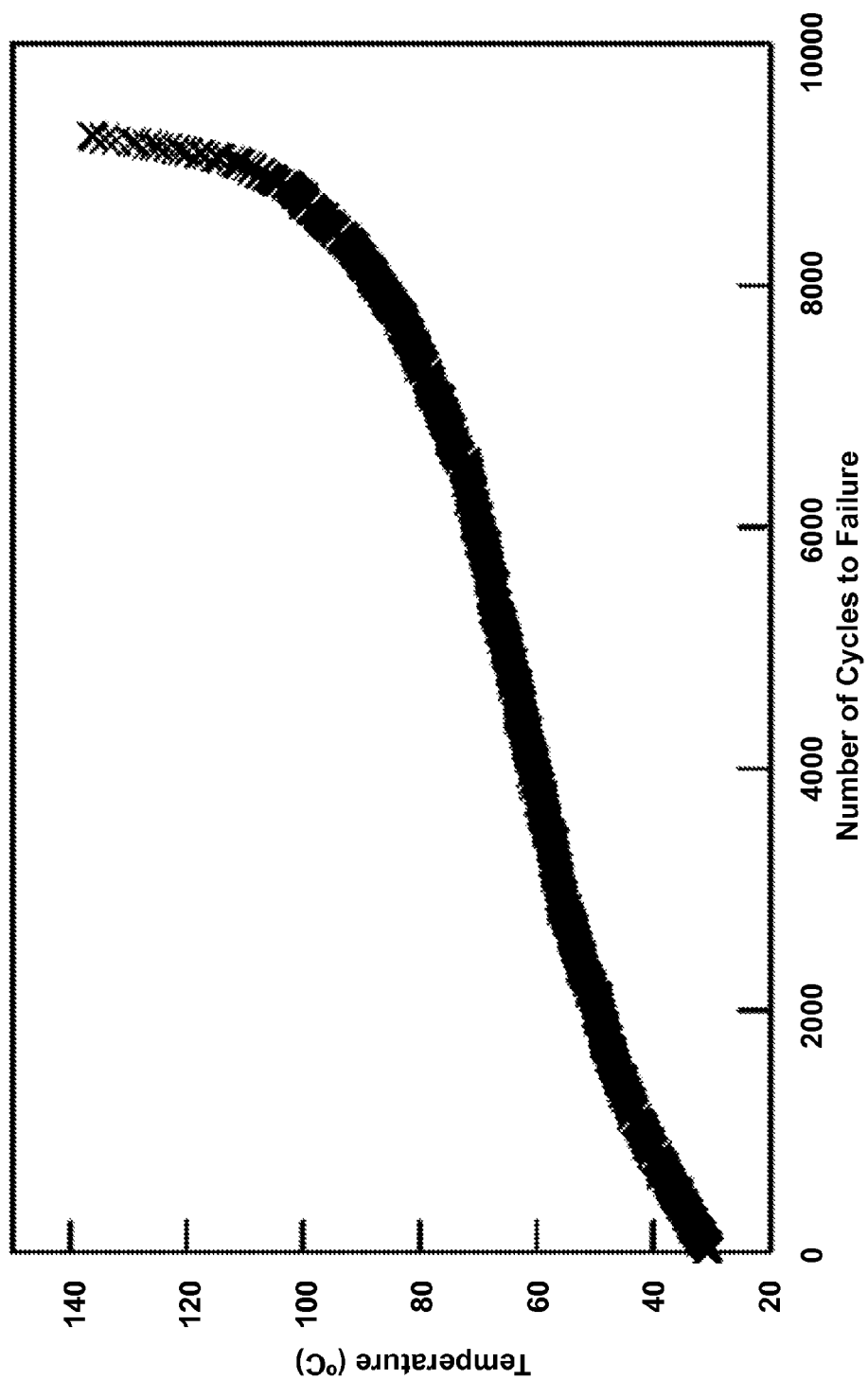
FIG. 9(a) depicts the typical temperature variation during the fatigue life of a glass/epoxy laminate for a 2.785 kN load amplitude, zero load ratio, frequency 10 Hz.

FIG. 9(a) depicts typical temperature variation during the fatigue life of the glass/epoxy laminate for a 2.785 kN load amplitude, zero load ratio, frequency 10 Hz. The temperature rapidly increased during the early stage of fatigue life due to matrix cracking, breaking of weaker fibers, and delamination at the weaker fiber/matrix interfaces. Once the damage reached a saturation level, a second stage of steady and slow increase began, followed by a third stage of sudden temperature rise due to the breaking of stronger fibers.

Example 13

Figure 9B:
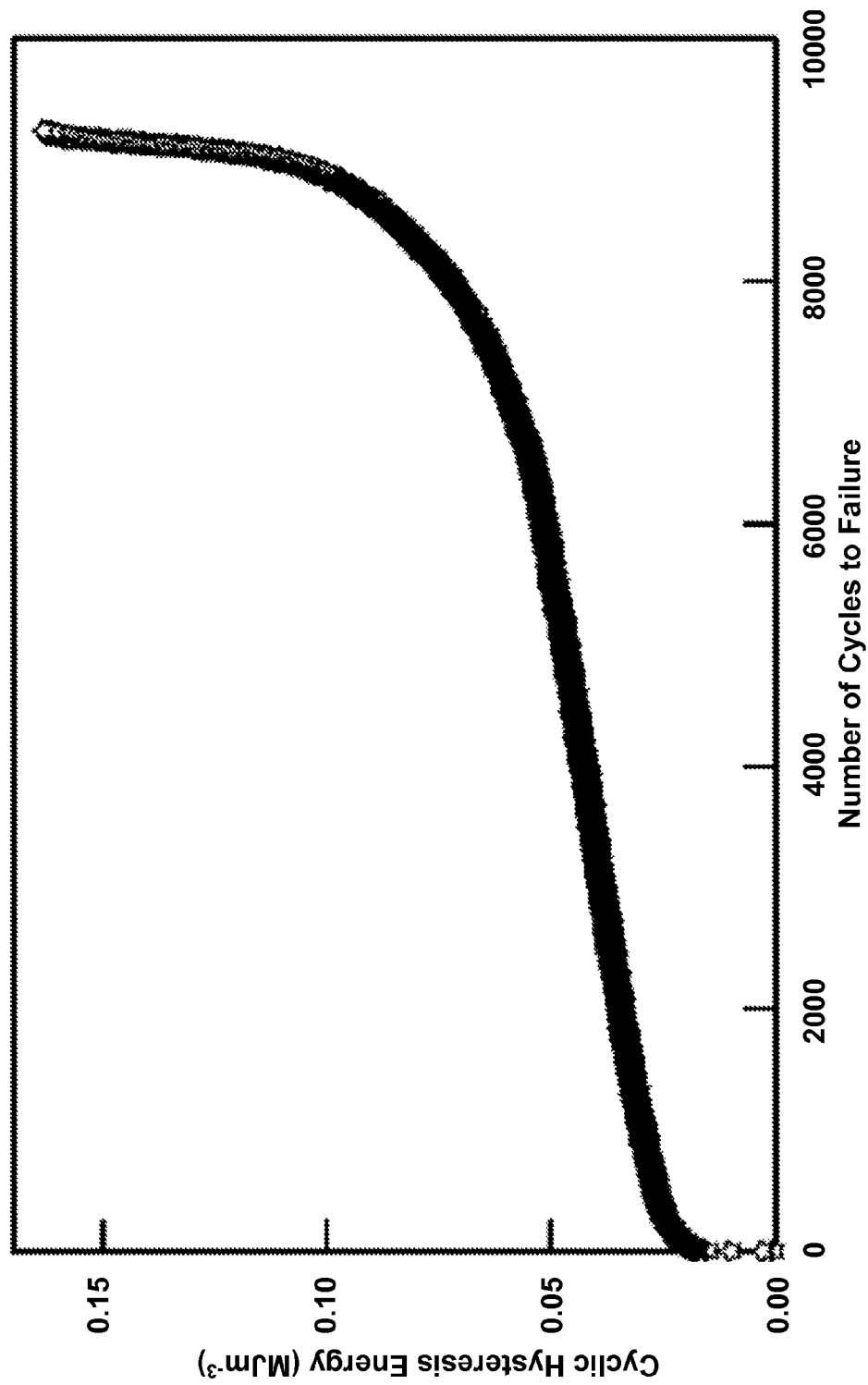
FIG. 9(b) shows typical hysteresis energy evolution for the same fatigue test as depicted in FIG. 9(a).

FIG. 9(b) shows a typical hysteresis energy evolution, for the same fatigue test as depicted in FIG. 9(a). Cyclic energy proceeded through three regimes: a rapid increase, a slow and steady increase, and a sudden rise before failure.

| | |
|---|---|
| w: cyclic hysteresis energy | θ: the angle between load direction and lengthwise direction |
| $w_r$: accumulated fracture energy | γ: entropy production |
| K: thermal conductivity | $\sigma_{1max}, \sigma_{2max}, \sigma_{6max}$: maximum stress component |
| $N_f$: number of cycles at failure | $\sigma_{1min}, \sigma_{2min}, \sigma_{6min}$: minimum stress component |
| R: load ratio | $\epsilon_{1max}, \epsilon_{2max}, \epsilon_{6max}$: maximum strain component |
| S: shear strength | $\epsilon_{1min}, \epsilon_{2min}, \epsilon_{6min}$: minimum strain component |
| T: temperature | $\epsilon_{1u}, \epsilon_{2u}, \epsilon_{6u}$: maximum static strain |
| X: static strength (lengthwise) | ΔW: normalized linear elastic energy |
| Y: static strength (crosswise) | |

TABLE 4

Experimental data of Mechanical properties of G10/FR4 laminate

| Tensile Strength (MPa) | | | | | | | Modulus of Elasticity (GPa) | | | | | | | Shear Strength (MPa) |
|---|---|---|---|---|---|---|---|---|---|---|---|---|---|---|
| 0° | 90° | 15° | 30° | 45° | 60° | 80° | 0° | 90° | 15° | 30° | 45° | 60° | 80° | |
| 375 | 320 | 253 | 190 | 210 | 235 | 234 | 19 | 17 | 15.5 | 7 | 3 | 6 | 15 | 170 |

Example 14

Figure 10:
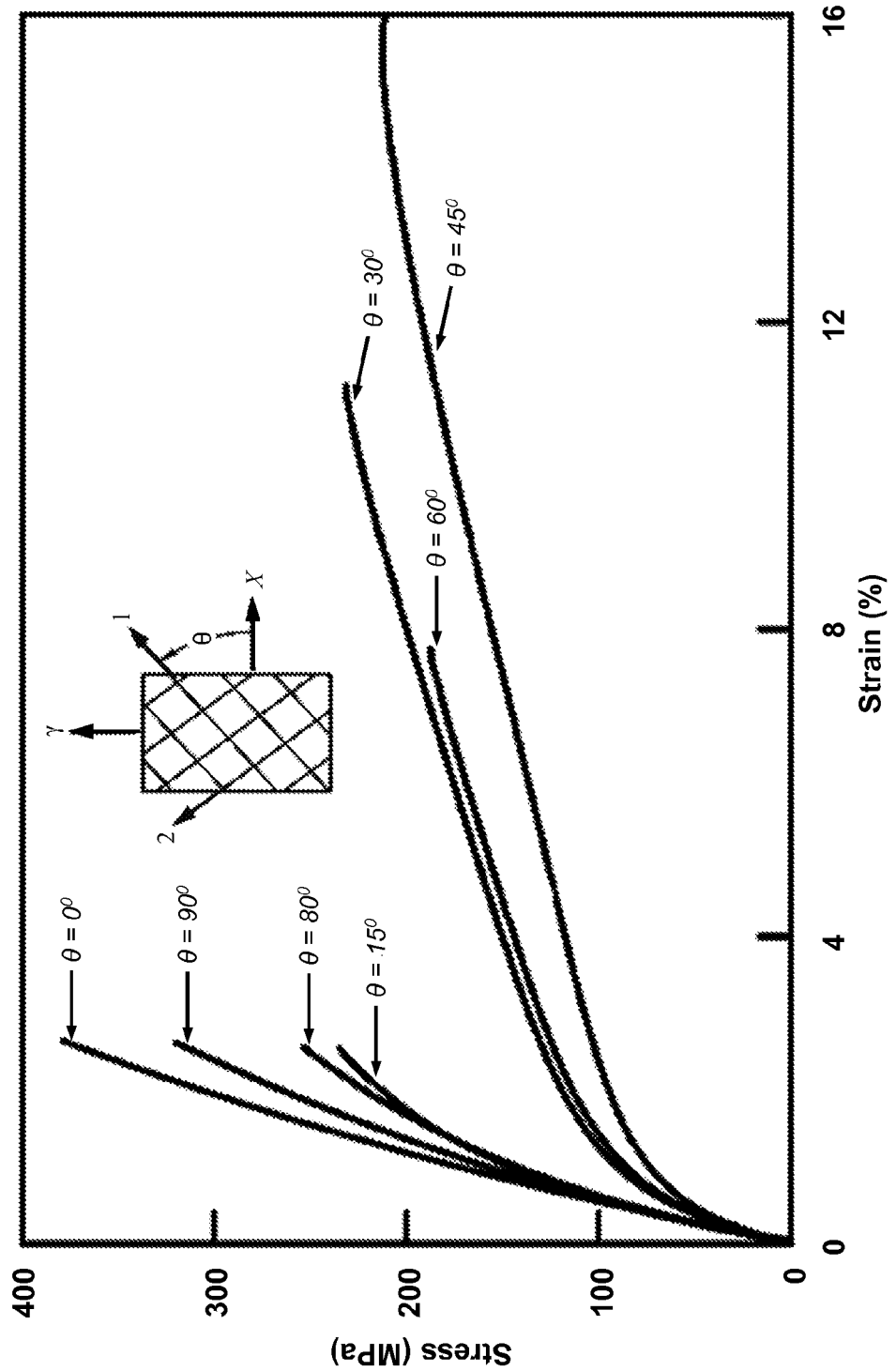
FIG. 10 depicts a plot of stress-strain for a Glass/Epoxy laminate subjected to a series of static tests for both on- and off-axis directions at room temperature.

FIG. 10 depicts a stress-strain plot for the Glass/Epoxy laminate (G10/FR4), subjected to a series of static tests in both on- and off-axis directions at room temperature. The stress-strain relationship on-axis was nearly linear before ultimate failure occurred. In the off-axis tests, an initial linear response was followed by a significant nonlinearity after only about 1% strain.

With on-axis loading, the load was primarily supported by the fibers, and failure stress was that of a normal stress. However, in off-axis loading the predominant failure mechanism was from shear stress, and material behavior was characterized by a combination of nonlinear elasticity and damage in the matrix and the fibers.

Figure 11:
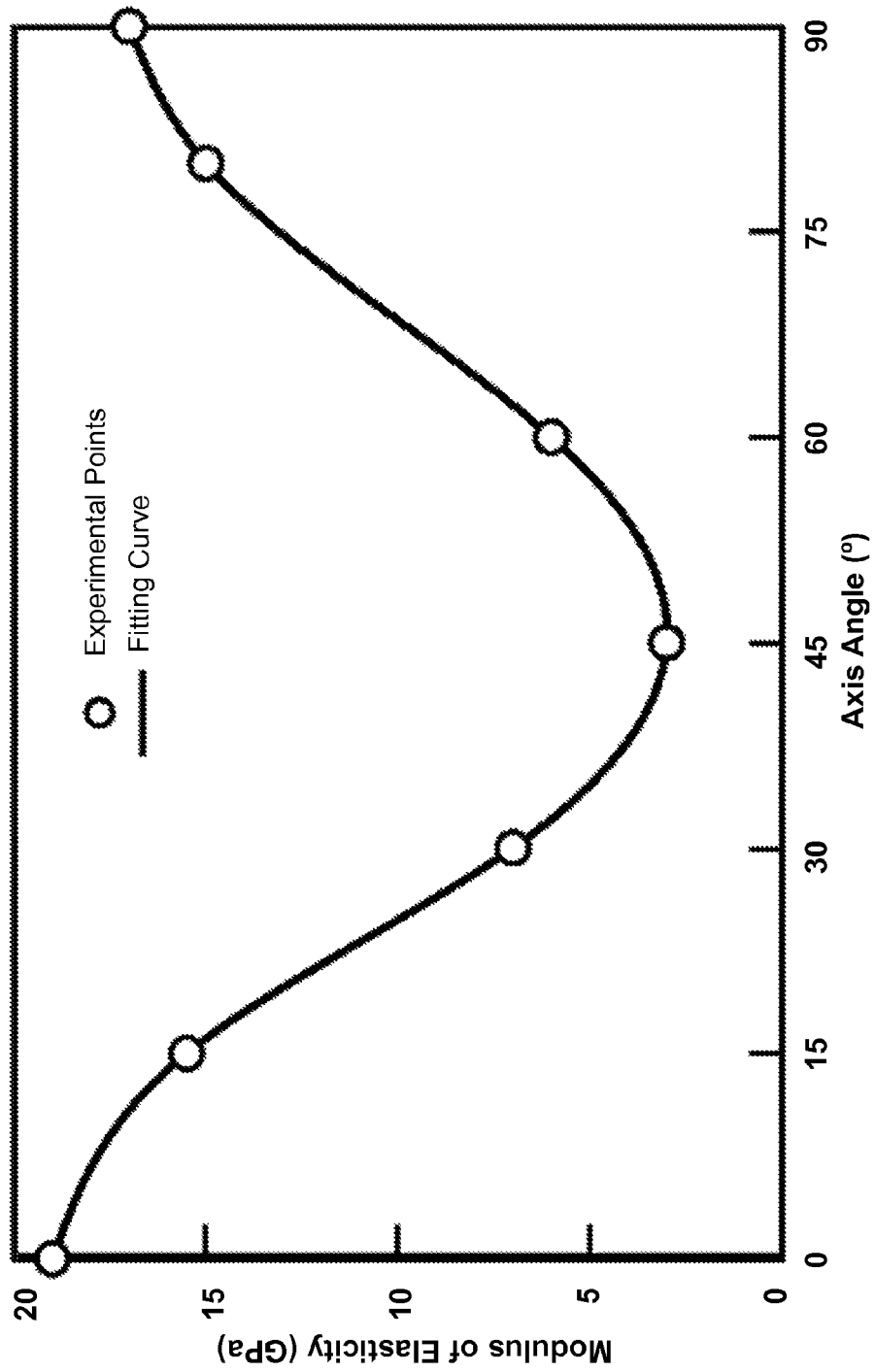
FIG. 11 depicts the variation of modulus of elasticity of a Glass/Epoxy laminate at different fiber angles.

FIG. 11 depicts the variation of the modulus of elasticity of Glass/Epoxy (G10/FR4) laminate at different fiber angles. It shows that as the off-axis angle increased, the magnitude of the elastic modulus decreased up to 45°. Beyond 45°, the elastic modulus began to increase.

Examples 15-19

Figure 12A:
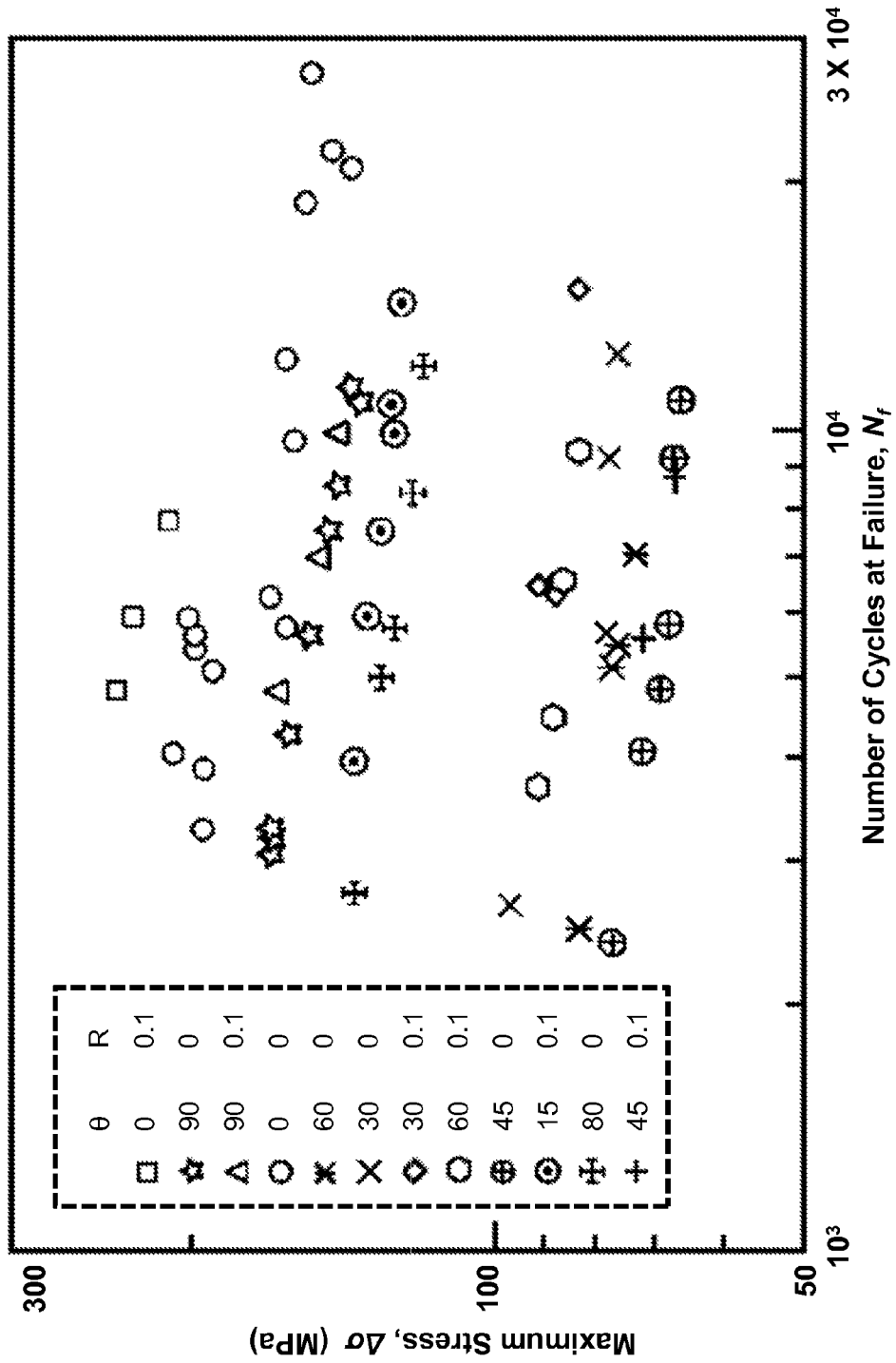
Figure 12B:
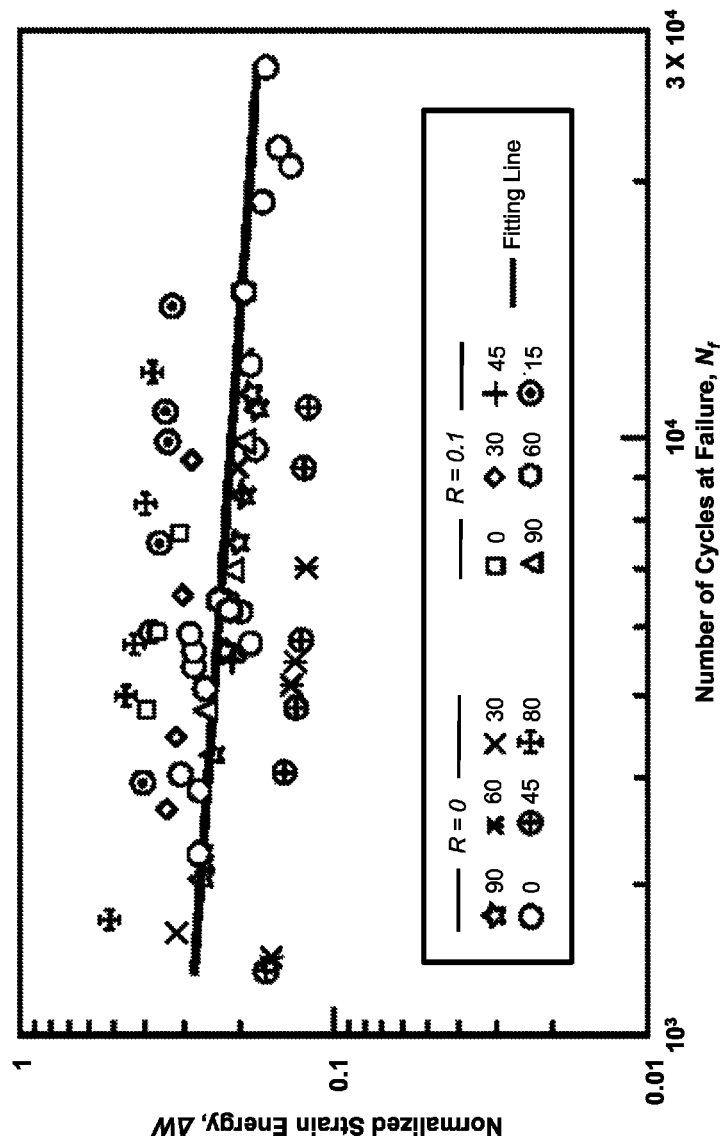
Figure 12D:
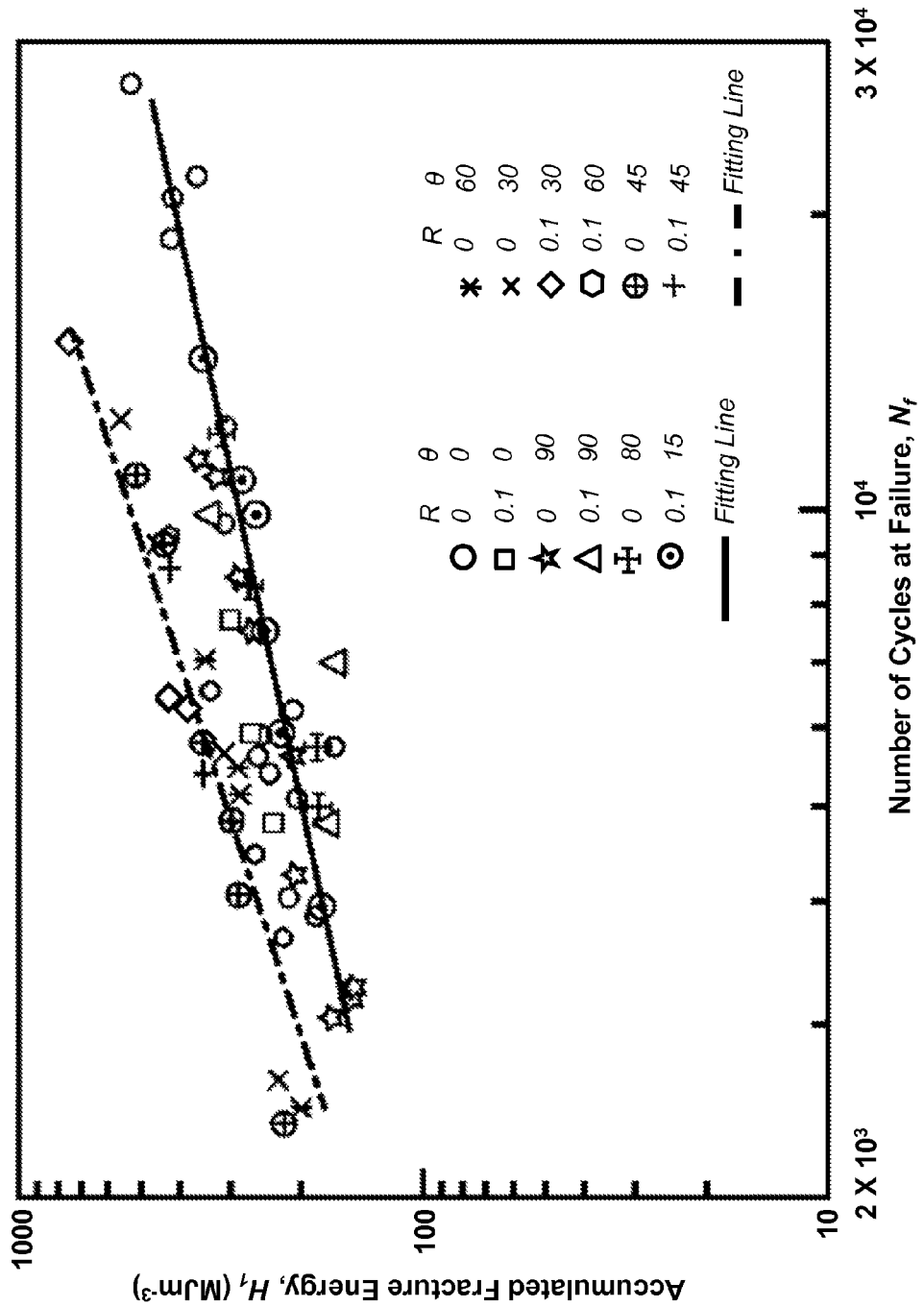
Figure 12E:
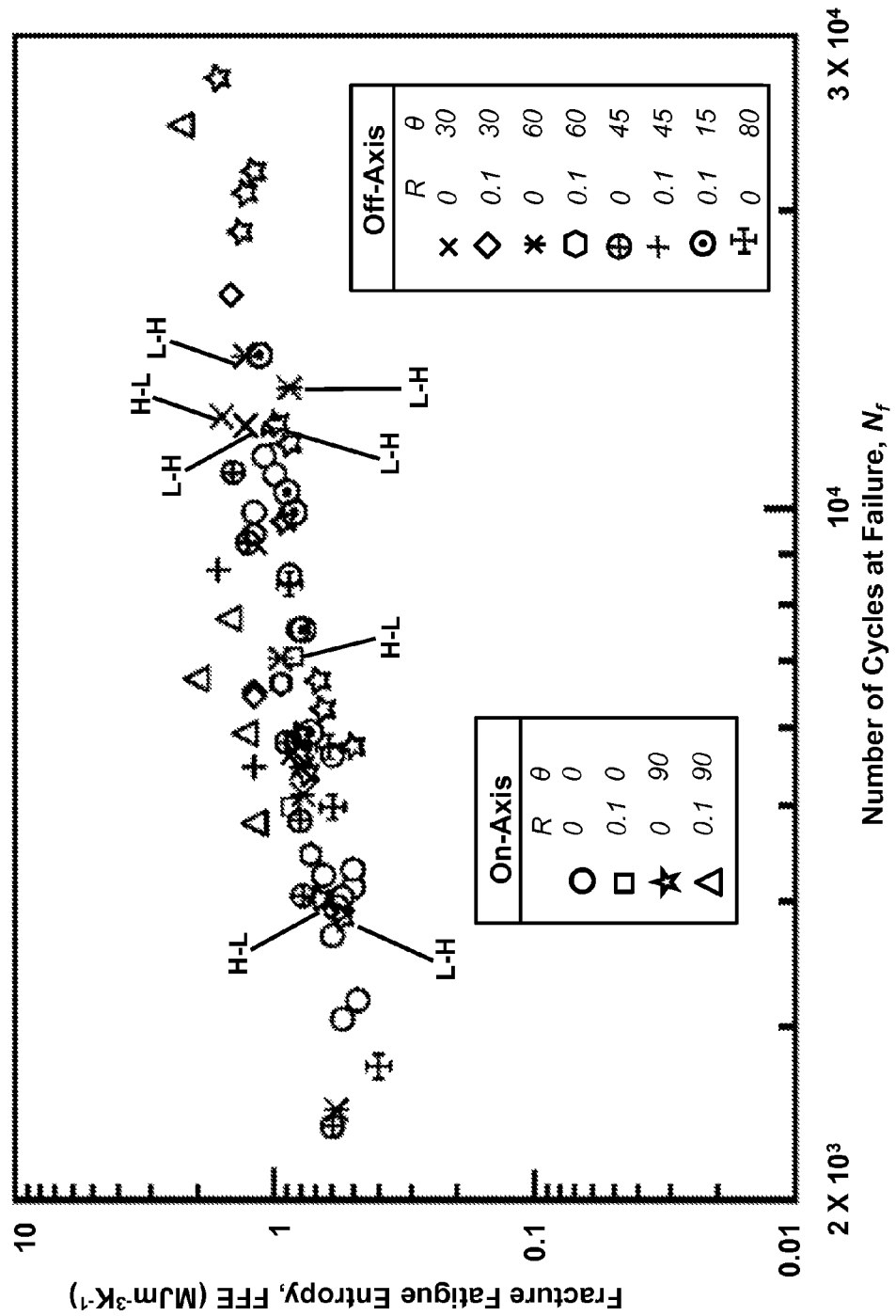

An extensive set of fatigue tests was conducted on the Glass/Epoxy laminate at different stress ratios (R=0 or 0.1), and load angles (θ=0, 15, 30, 45, 60, 80, 90°), all at a frequency of 10 Hz. These measurements were fitted to three models, as depicted in FIGS. 12(a)-(e): FIG. 12(a) depicts the stress life approach. FIG. 12(b) depicts the elastic strain energy method. FIG. 12(c) depicts the cyclic hysteresis energy method. FIG. 12(d) depicts the accumulated fracture energy method. FIG. 12(e) depicts the fracture fatigue entropy model. H-L: High-to-Low load, L-H: Low-to-High load.

As shown in FIG. 12(a), the fatigue life depended strongly on both the fiber load angle and the stress ratio. Data scatter was relatively large.

The experimental results were fitted to the models of Equations (1), (2), and (3) for the number of cycles at failure, by least squares fit. FIG. 12(b) depicts least-squares fit for normalized strain energy versus the number of cycles at failure. The derived relationship was:

$$\Delta W = 1.2064 N_f^{-0.189} \tag{21}$$

with the "goodness of fit," $R_g^2 = 0.8$.

FIG. 12(c) depicts results for cyclic hysteresis energy at the time of failure. It showed a similar trend as that strain energy method. The best fitting curve had an $R_g^2 = 0.82$:

$$H = 4.8262 N_f^{-0.444} \tag{22}$$

FIG. 12(d) depicts the accumulation of hysteresis energy obtained up to the time of failure. The data for load angles close to the crosswise angle (90°) and to the lengthwise angle (0°) were distributed around the curve:

$$H_t = 2.4413 N_f^{0.5199} \tag{23}$$

with the goodness of fit $R_g^2 = 0.83$.

By contrast, the fatigue life at a high load angle (30, 45, 60°) showed a different relationship:

$$H_t = 1.2415 N_f^{0.6497} \tag{24}$$

with the goodness of fit $R_g^2 = 0.88$. The reason for the difference can be attributed to the fatigue properties of the Glass/Epoxy laminate at different load angles. The plot of stress-strain at load angles close to the crosswise or lengthwise direction was almost linear; and failure was dominated by normal stress. However, at angles of 30, 45, and 60° the failure was dominated by shear stress, and the observed stress-strain behavior was highly nonlinear.

FIG. 12(e) depicts a plot of fracture fatigue entropy versus cycle number at failure. In this set of experiments, a necessary and sufficient condition for the final fracture of the Glass/Epoxy laminate being tested was that there should have been an entropy gain between approximately 0.4 MJm$^{-3}$K$^{-1}$ and 2.5 MJm$^{-3}$K$^{-1}$ for various on- and off-axis angles. There was less scatter in the plotted data, as compared to that plotted for the prior methods.

Example 20

The invention may be used, for example, in predicting and preventing the catastrophic failure of composite materials from fatigue load. We have discovered that the entropy generated during the fatigue life accumulates as it approaches the final value, $\gamma_f$, at which the composite fails. Fracture fatigue entropy, FFE, is useful as an index of failure. As the accumulated entropy generation accumulates toward the expected FFE, the composite may be taken out of use, the machine may be shut down, etc. before catastrophic failure occurs.

Example 21

In a preferred embodiment, cyclic entropy production is measured in real time by transmitting temperature measurements from the surface of a composite to a programmed computer that determines and compares accumulated entropy production to the expected FFE value at failure. The calculations may be used to estimate the expected remaining life of the composite material. The system can then automatically halt operations before catastrophic failure occurs, for example, when 90% of the expected FFE has been reached; or at a value specified by the user.

Example 22

To illustrate one use of this invention, refer to FIG. 12e, which plots FFE as a function of the number of cycles to failure. The FFE at which failure occurs is about 0.3. A user of the invention can specify a limiting value of the expected FFE at failure, for example 80%, 85%, 90%, or 95% of the expected FFE at failure, depending on individual considerations of cost and benefit a particular situation. For example, if the limiting value is set at 90% of the expected 0.3 FFE at failure, then halting operations at an FFE of 0.27 will avoid catastrophic failure in most cases. (See Example 23 for a description of a system that may be used for this monitoring.) By contrast, the conventional stress-based results (e.g., FIG. 12a) do not provide a good mechanism for monitoring the health of a machine or component.

Example 23

Figure 13:
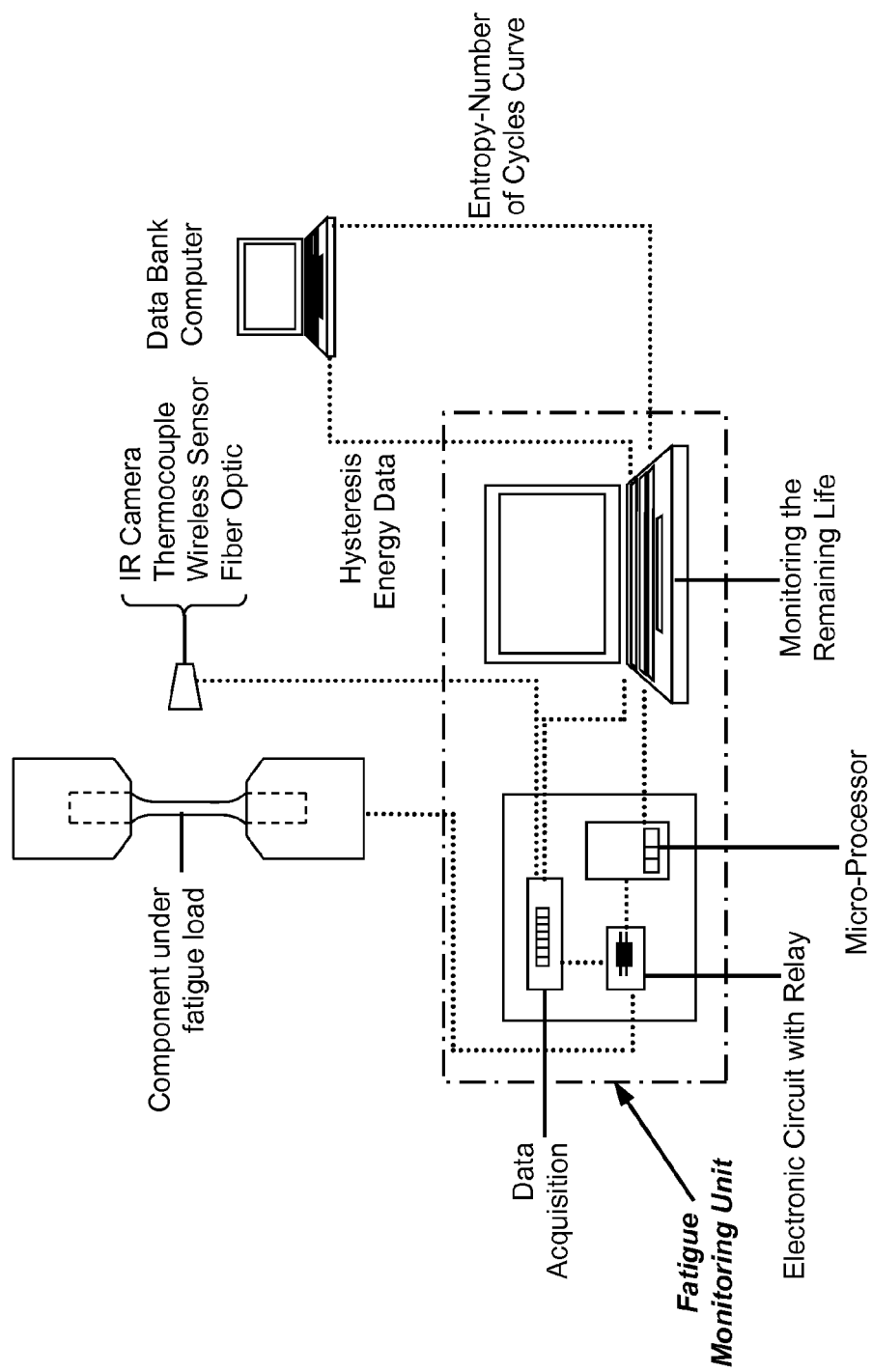
FIG. 13 schematically depicts a device for monitoring composite material life.

FIG. 13 schematically depicts a device for monitoring the lifetime of a composite material subjected to cyclic fatigue. A processor calculates the accumulation of entropy during the operations. Temperature measurements are captured by a sensor (e.g., a thermocouple, IR camera, or fiber optic). Temperature measurements are transferred either by wire or wirelessly to the data acquisition system of the monitoring unit. The calculated entropy is compared with the lower FFE limit of the entropy—cycles curve in real time (e.g., as in FIG. 12e). Once the accumulated entropy reaches the limiting value of the entropy or a user-defined fraction of the limiting entropy, a signal is sent to a relay that halts the operation of the machine under fatigue loading.

There are "extraneous" factors that can affect the actual or apparent measured value of FFE and FFE at failure, including for example, ambient temperature, corrosive conditions, etc. The best results will be obtained when "benchmark" FFE measurements are carried out under conditions that match as closely as possible the conditions of actual use.

Any of the various techniques or sensors known in the art may be used to measure temperatures for use in the novel method, including for example infrared thermal imaging, thermocouples, resistance thermometers, pyrocouple sensors, and the like. It is especially important to monitor temperatures near the point (or region) of incipient failure.

The complete disclosures of all references cited in this specification; and the complete disclosure of the priority application, Ser. No. 61/446,845; and the complete disclosures of all references cited in priority application Ser. No. 61/446,845 are all hereby incorporated by reference in their entirety. Also incorporated by reference is the following publications by the inventors and their colleagues: Naderi, M. and Khonsari, M. M. "Real-time Fatigue Life Monitoring based on Thermodynamic Entropy," *Journal of Structure Health Monitoring*, v. 10, pp. 189-197 (2010); Naderi, M. et al., "Dissipated Thermal Energy and Damage Evolution of Glass/Epoxy Using Infrared Thermography and Acoustic Emission," *Composites Part B: Engineering*, dx.doi.org/10.1016/j.compositesb.2011.08.002 (2011); Naderi, M. and Khonsari, M. M., "A Comprehensive Fatigue Failure Criterion Based on Thermodynamic Approach," *J. Compos. Mat.*, vol. 46, pp. 437-447 (2012); Naderi, M. and Khonsari, M. M., "Thermodynamic Analysis of Failure Fatigue in a Composite Laminate," Mechanics of Materials, vol. 46, pp. 113-122 (2012); Amiri, M. and Khonsari, M. M., "On the role of entropy generation in processes involving fatigue," *Entropy*, vol. 14, pp. 24-31 (2012). In the event of an otherwise irreconcilable conflict, however, the present specification shall control.

What is claimed:

1. A method for preventing mechanical failure of a composite material, wherein the composite material is solid-state and inhomogeneous; wherein the composite material is subject to cyclic loading; and wherein said method comprises the following steps:
   (a) measuring the temperature of the surface of the composite material, in the vicinity of a location of incipient mechanical failure, using a temperature sensor;
   (b) approximating the accumulated volumetric entropy production γ in the vicinity of the location of incipient mechanical failure of the composite material, using a processor to approximate the numerical value of γ, using a relationship that is equivalent to:

$$\gamma = \int_0^{t'} \left(\frac{w}{T} + \frac{e_d}{T}\right) dt$$

wherein t denotes the time, t' denotes the particular time for which γ is being determined, T denotes the temperature of the surface of the composite material in the vicinity of the location of incipient mechanical failure, w denotes the rate of volumetric work of permanent deformation for the composite material, and $e_d$ denotes the damage energy;
   (c) predicting mechanical failure of the composite material when a processor determines that γ is approaching the value of $\gamma_f$, or is approaching a user-specified fraction of the value of $\gamma_f$, wherein $\gamma_f$ denotes the mean volumetric fracture fatigue entropy for the composite material; and
   (d) stopping the cyclic loading of the composite material, using a controller, when γ approaches the value of $\gamma_f$, or when γ approaches a user-specified fraction of the value of $\gamma_f$.

* * * * *